(12) United States Patent
Nishi et al.

(10) Patent No.: US 8,951,183 B2
(45) Date of Patent: *Feb. 10, 2015

(54) NEUROTROPHIC FACTOR PRODUCTION PROMOTING DEVICE

(71) Applicant: P-Mind Co., Ltd., Kumamoto (JP)

(72) Inventors: Mitsuharu Nishi, Kumamoto (JP); Iwao Kishita, Kumamoto (JP)

(73) Assignee: P-Mind Co., Ltd., Kumamoto-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/027,319

(22) Filed: Sep. 16, 2013

(65) Prior Publication Data

US 2014/0081073 A1    Mar. 20, 2014

Related U.S. Application Data

(63) Continuation of application No. 12/514,080, filed as application No. PCT/JP2006/322295 on Nov. 8, 2006, now Pat. No. 8,562,506.

(51) Int. Cl.
*A61N 1/00* (2006.01)
*A61N 2/00* (2006.01)
*A61N 2/02* (2006.01)
*A61N 1/40* (2006.01)

(52) U.S. Cl.
CPC ............... *A61N 2/006* (2013.01); *A61N 2/004* (2013.01); *A61N 2/02* (2013.01); *A61N 1/40* (2013.01)
USPC .......................................................... 600/14

(58) Field of Classification Search
USPC ..................................... 600/9–15
See application file for complete search history.

(56) References Cited

U.S. PATENT DOCUMENTS 6,132,361 A    10/2000    Epstein et al.
6,425,851 B1    7/2002    Kiontke
(Continued)

FOREIGN PATENT DOCUMENTS

DE         4309395         9/1993
DE    197 52 934 A1    12/1998
(Continued)

OTHER PUBLICATIONS

Fujiki, M., "Magnetic Stimulation of the Brain", The Magnetics Society of Japan Kenkyukai Shiryo, (125th) pp. 3-10 (2002) (with English abstract).

(Continued)

*Primary Examiner* — John Lacyk
(74) *Attorney, Agent, or Firm* — Oblon, Spivak, McClelland, Maier & Neustadt, L.L.P.

(57) ABSTRACT

A device to promote the production of neurotrophic factor without transplantation of cells or injection into the affected area is provided. The device contains a high frequency electromagnetic wave generating means generating a high frequency electromagnetic wave. The magnetic stimulation by the high frequency alternating electromagnetic field allows the intracellular concentration of calcium ions to increase to induce exocytosis of the neurotrophic factor group and to increase mRNA of the neurotrophic factor group in the cells so that the synthesis and extracellular release of the neurotrophic factor group are promoted. The device is suitable for use in preventing or treating various diseases such as brain diseases.

15 Claims, 12 Drawing Sheets

(56) References Cited

U.S. PATENT DOCUMENTS

| | | | |
|---|---|---|---|
| 6,425,852 B1 | 7/2002 | Epstein et al. | |
| 8,562,506 B2 * | 10/2013 | Nishi et al. ..................... | 600/14 |
| 2003/0028071 A1 | 2/2003 | Handy et al. | |
| 2004/0077921 A1 | 4/2004 | Becker et al. | |
| 2004/0210282 A1 | 10/2004 | Flock et al. | |
| 2006/0142748 A1 | 6/2006 | Foreman et al. | |
| 2006/0212077 A1 | 9/2006 | Pilla et al. | |

FOREIGN PATENT DOCUMENTS

| | | |
|---|---|---|
| DE | 103 57 265 A1 | 7/2005 |
| EP | 0 500 983 A1 | 9/1992 |
| GB | 1 595 121 | 8/1981 |
| JP | 2 11170 | 1/1990 |
| JP | 2000 504966 | 4/2000 |
| JP | 2004 511314 | 4/2004 |
| JP | 2006 94940 | 4/2006 |
| WO | WO 97/13549 A1 | 4/1997 |
| WO | WO 99/01178 A1 | 1/1999 |
| WO | WO 2007/141874 A1 | 12/2007 |

OTHER PUBLICATIONS

Funamizu, H., "The Effects of rTMS on rat brain cells", The Institute of Electrical Engineers of Japan Magnetics Kenkyukai Shiryo, pp. 17-20 (2002) (with English abstract).

Okada, T., "ECT to TMS No Sayo Kijo—Seikagakuteki Kenkyu Kara-", Japanese Journal of Clinical Psychiatry, vol. 32, No. 3, pp. 245-251 (2003).

European Office Action issued Dec. 14, 2011 in patent application No. 06 823 199.2.

Extended European Search Report issued Aug. 22, 2011 in patent application No. 06823199.2.

Office Action as received in the corresponding Chinese Application No. 201010546497.9 dated Mar. 25, 2013 w/English Translation.

European Search Report as received in the corresponding European patent Application No. 13155709.2-1652 dated Apr. 3, 2013.

Office Action issued Feb. 3, 2014 in European Patent Application No. 13 155 709.2.

Office Action issued on Dec. 9, 2013 in Chinese Patent Application No. 201010546497.9 (with partial English language translation).

* cited by examiner

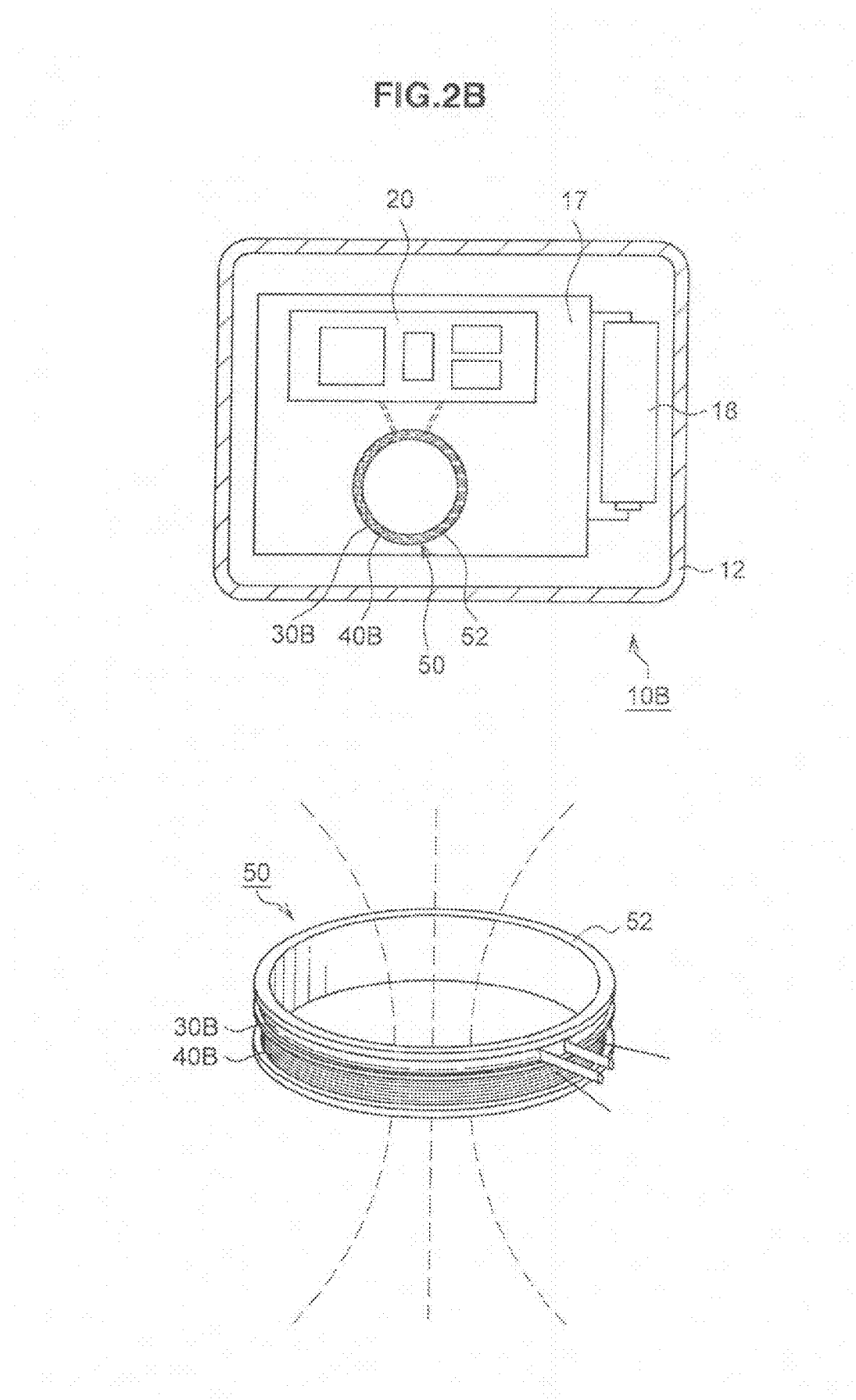

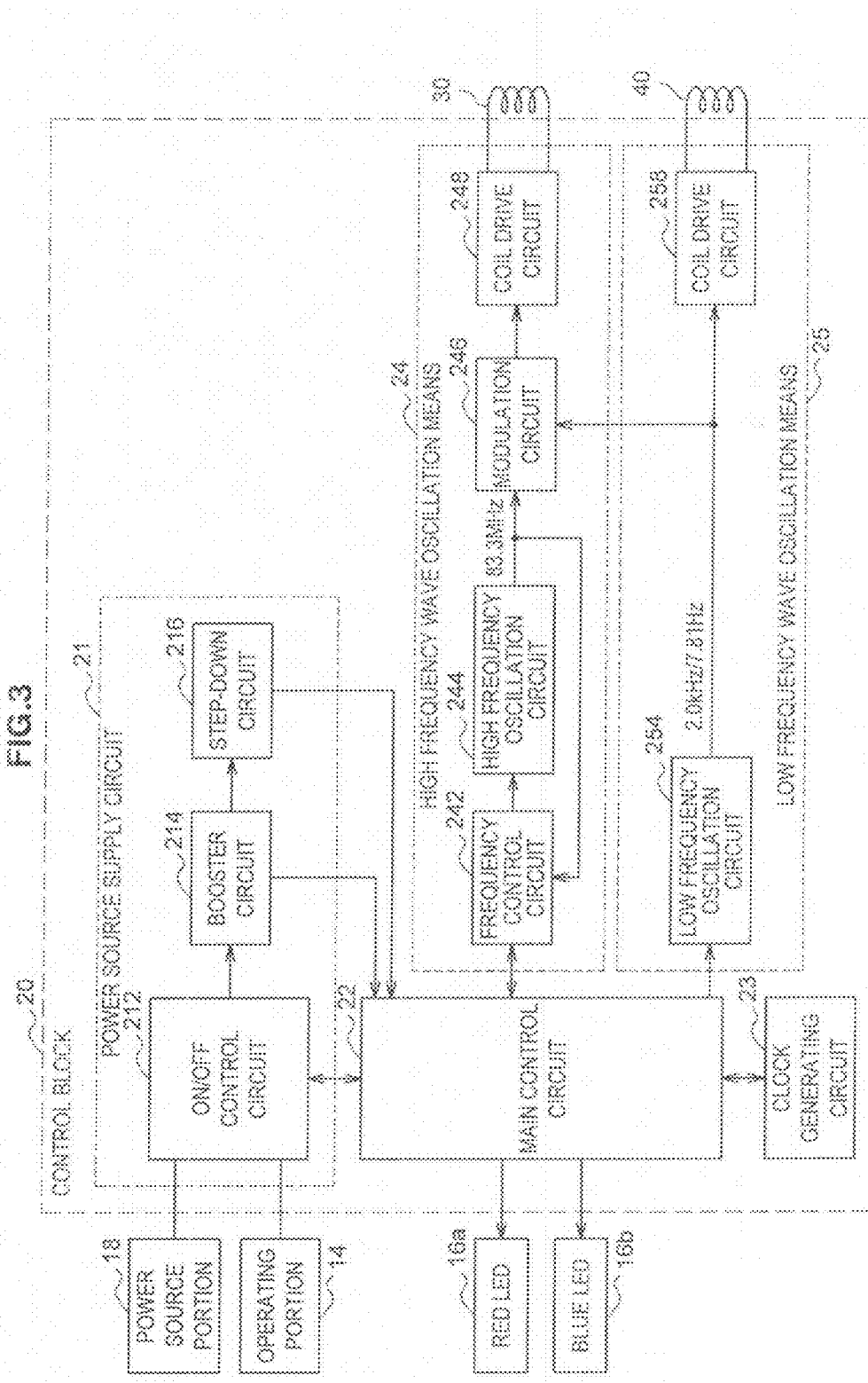

FIG.5A
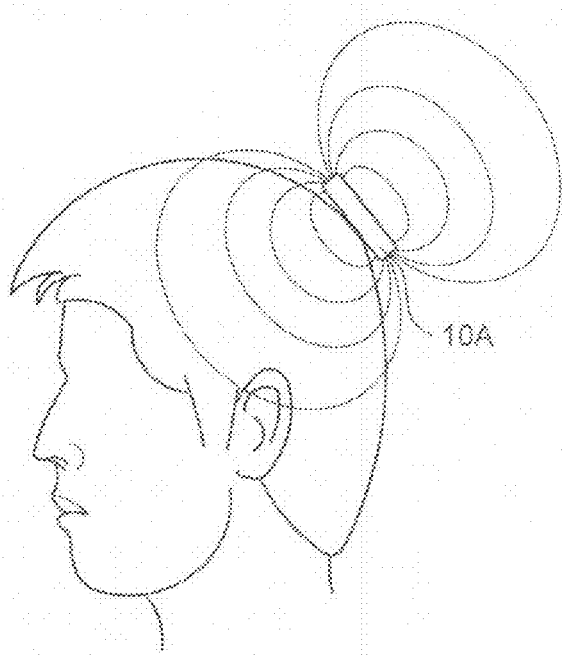
(a)
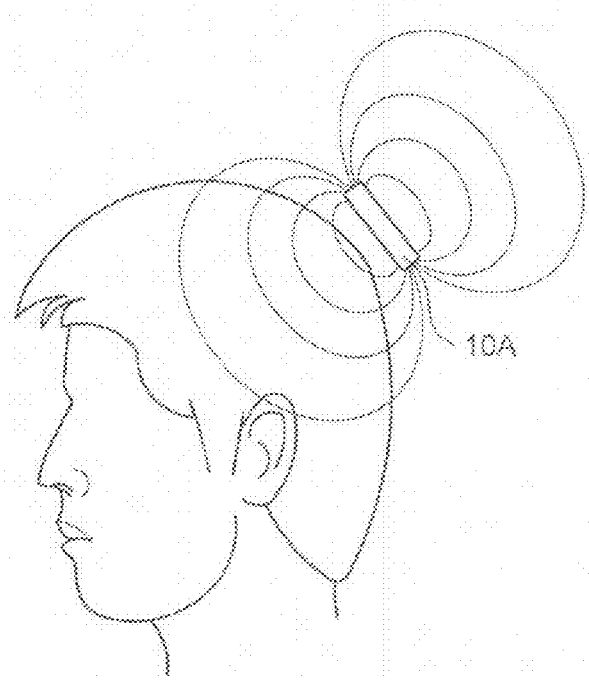
(b)

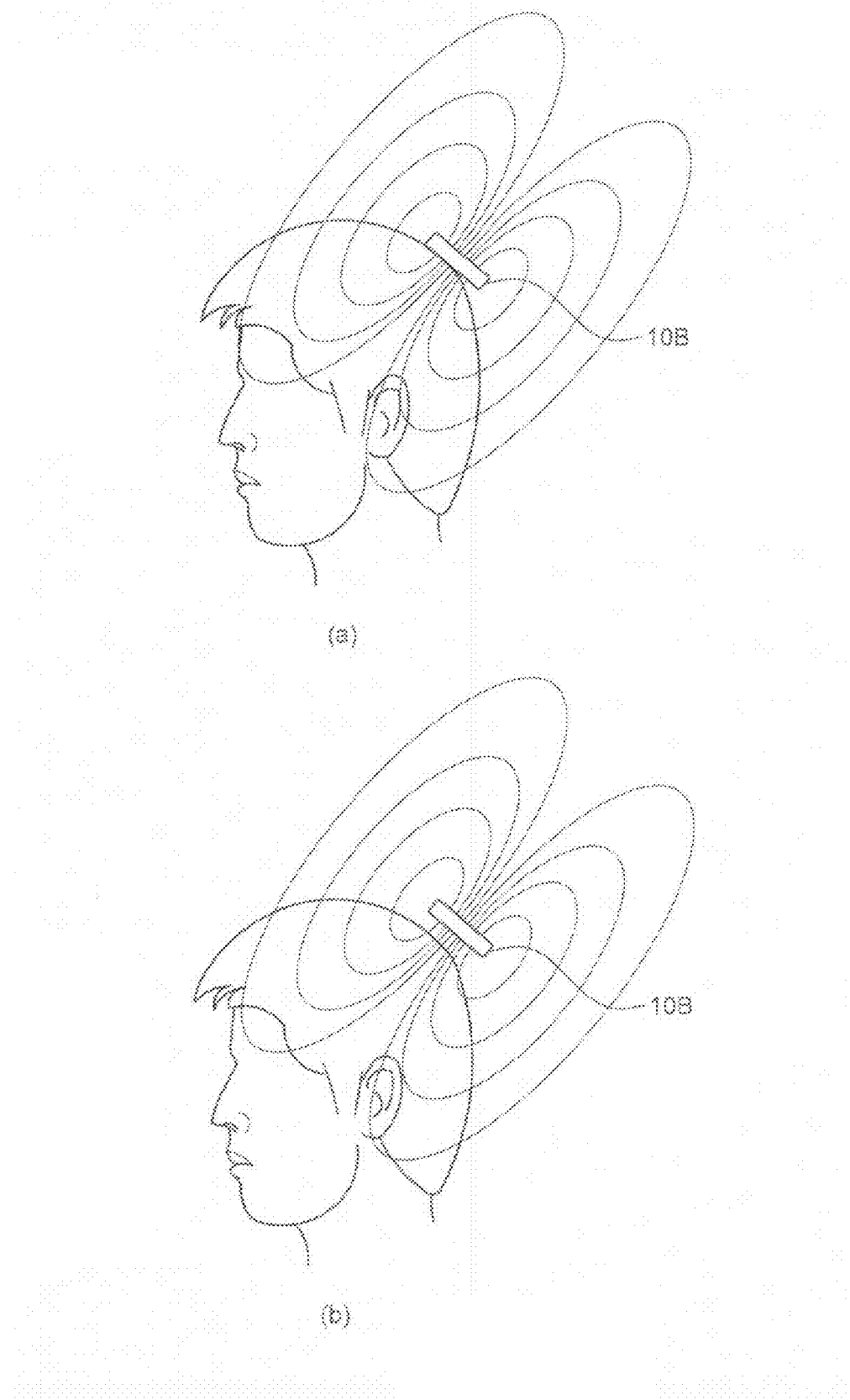

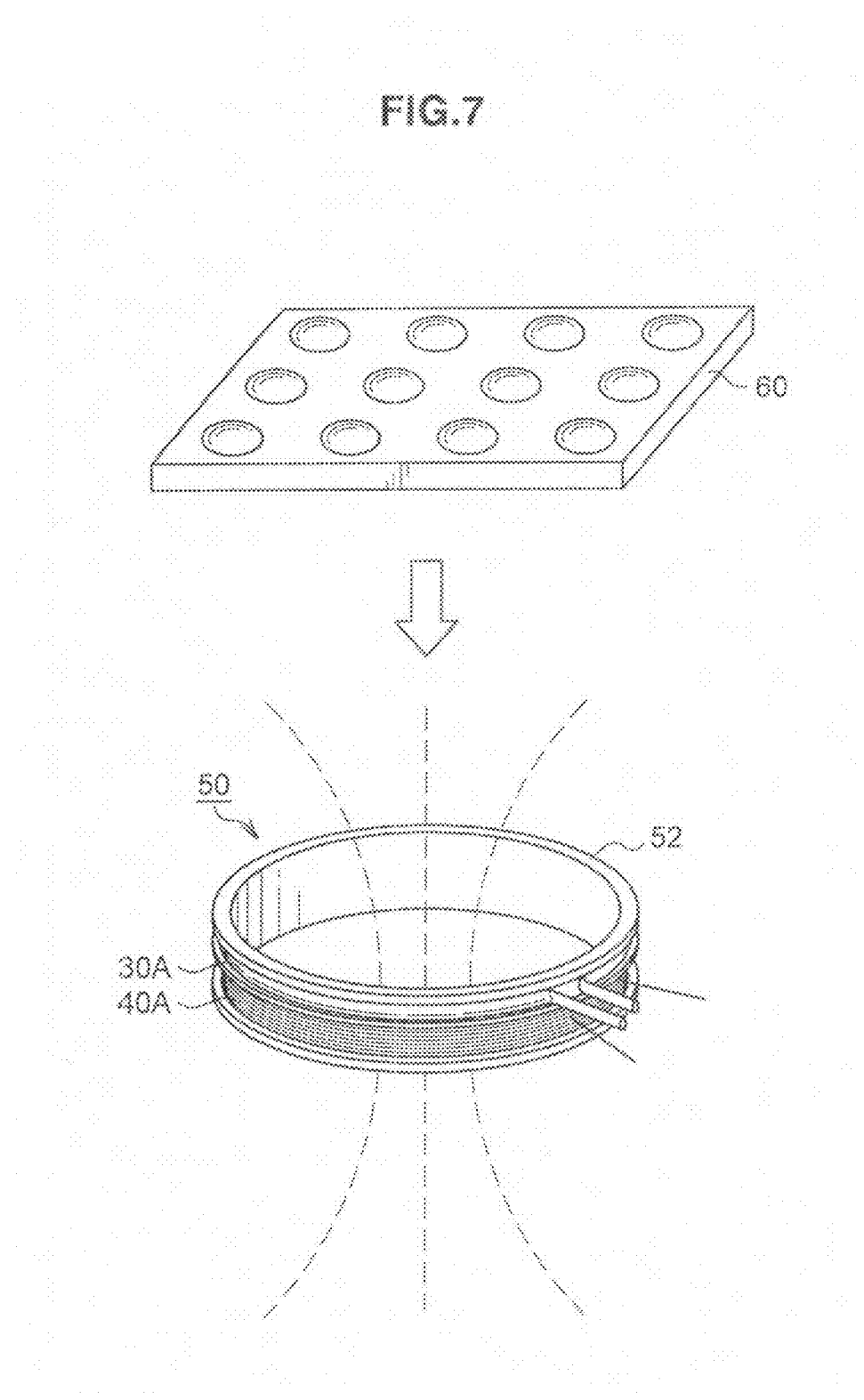

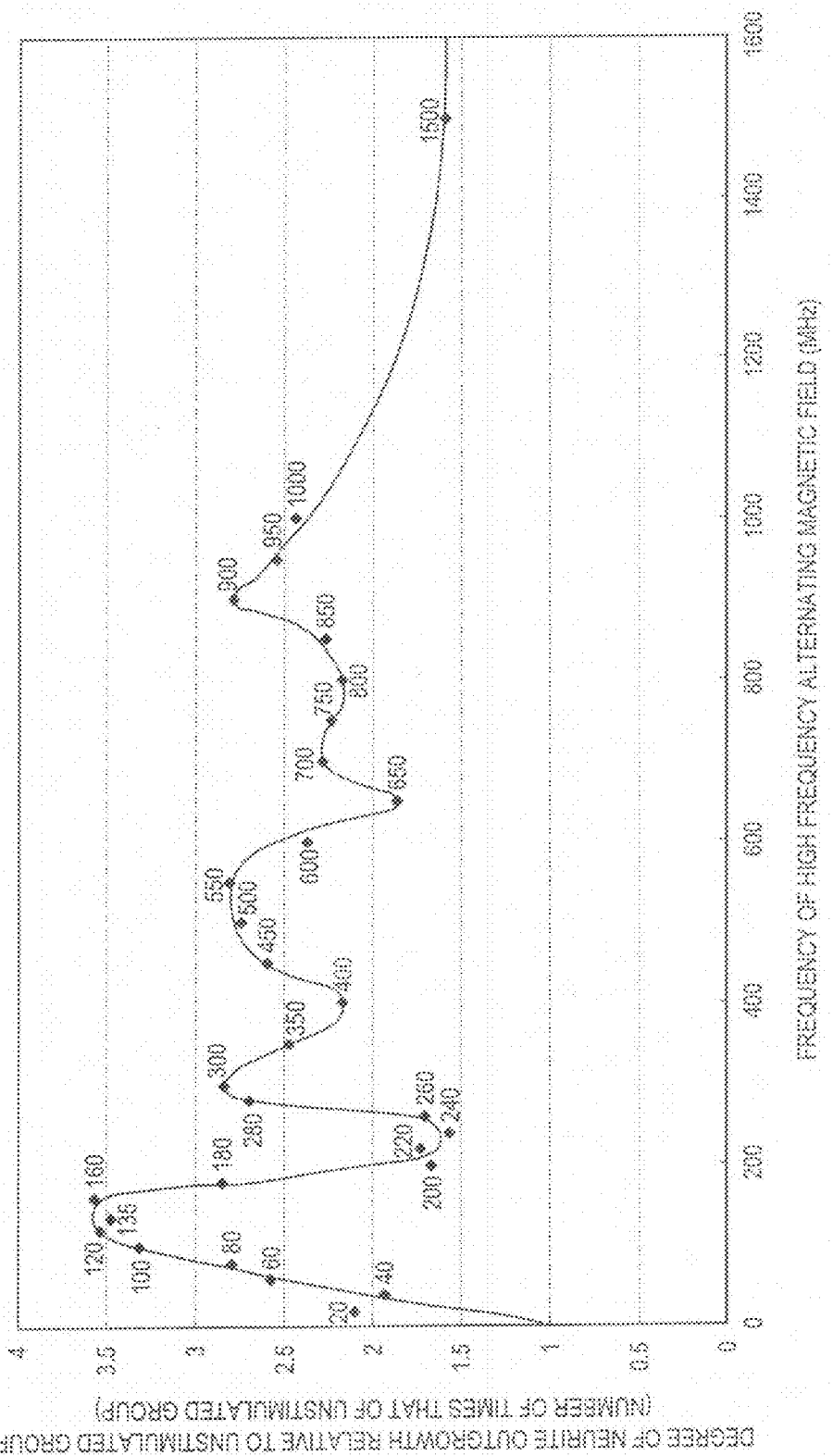

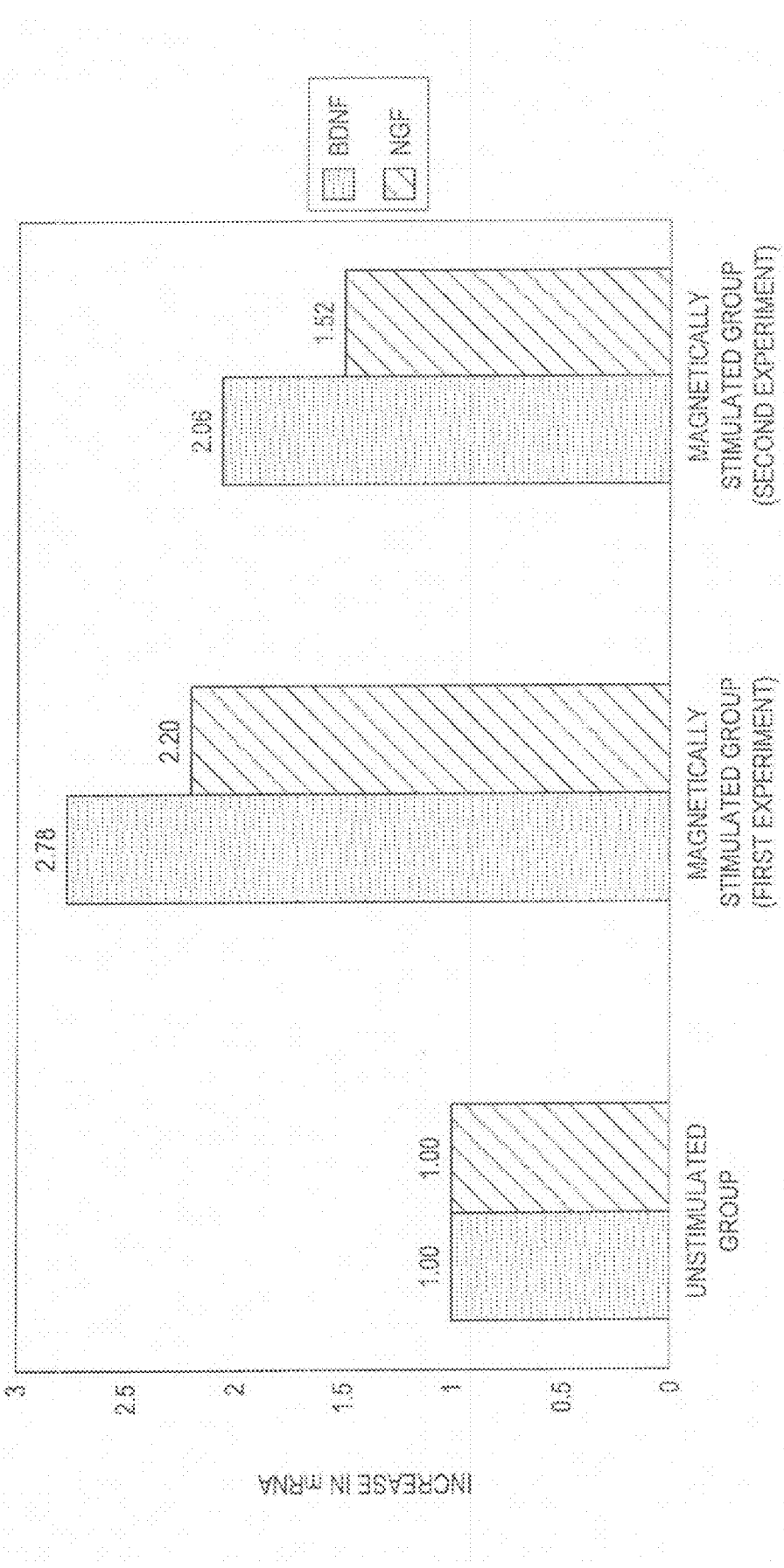

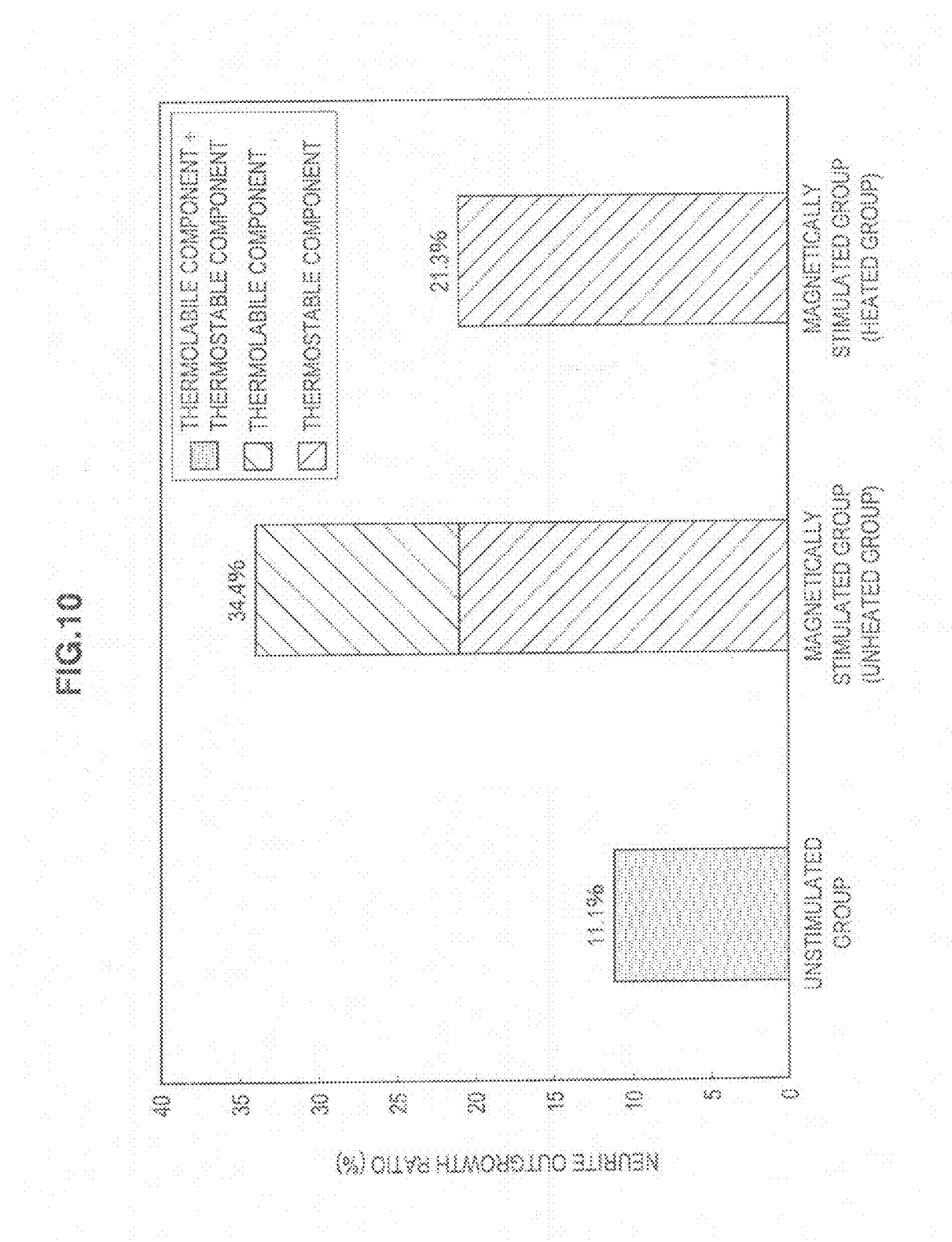

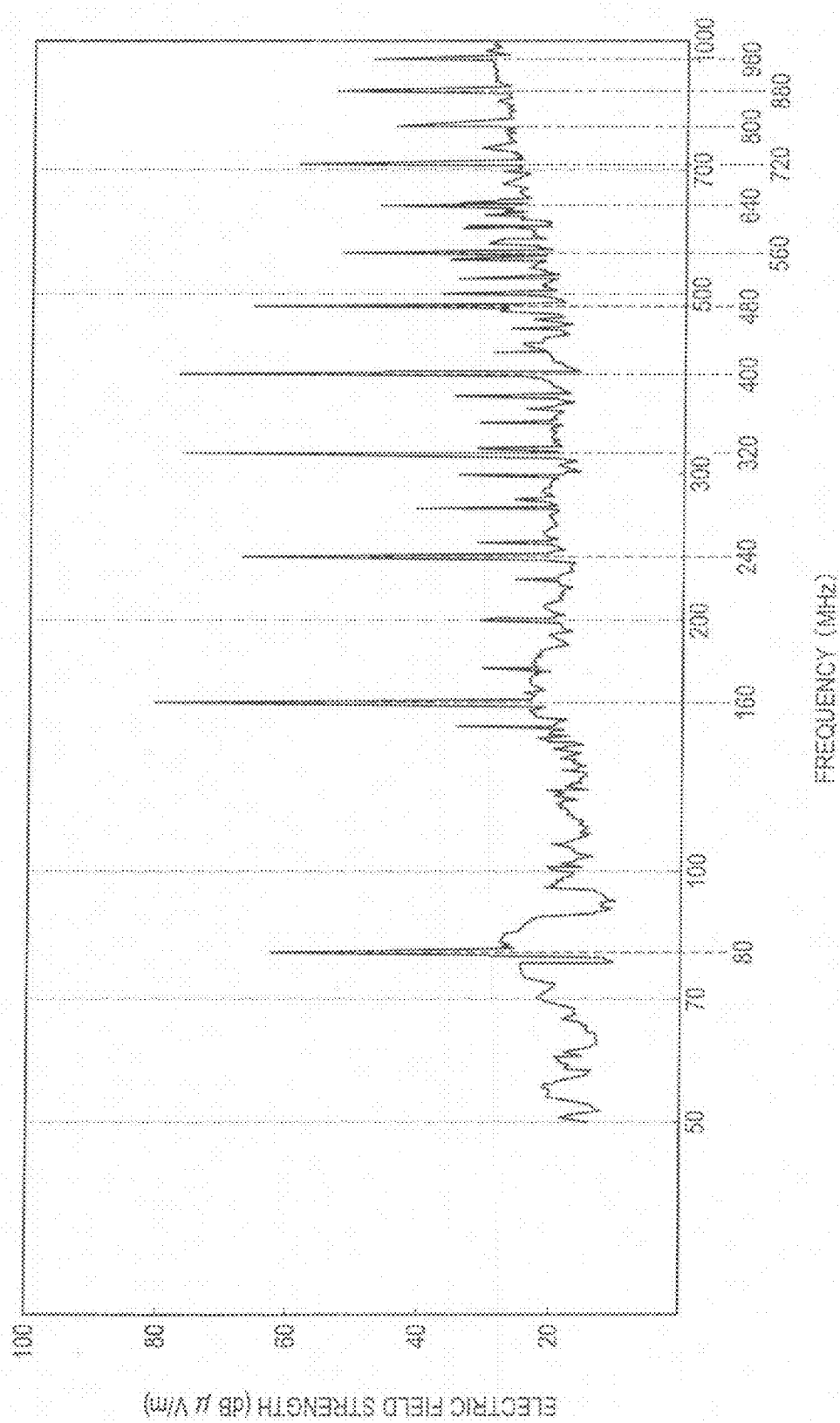

NEUROTROPHIC FACTOR PRODUCTION PROMOTING DEVICE

This application is a continuation of U.S. application Ser. No. 12/514,080 filed Jun. 19, 2009, now U.S. Pat. No. 8,562,506, which is a 371 of PCT/JP2006/322295 filed Nov. 8, 2006, the entire content of which is incorporated herein by reference.

TECHNICAL FIELD

The present invention relates to a neurotrophic factor production promoting device for promoting the production of a neurotrophic factor or a neurotrophic factor-like substance, which is useful in the treatment of various disorders such as brain diseases.

BACKGROUND ART

Brain diseases such as cerebrovascular disease, depression, and neurodegenerative disorder such as Alzheimer's disease are caused by a weakening of or damage to the central nervous system cells. In order for these brain diseases to be treated, research is being conducted on regenerative therapies of the brain in which damaged neurocytes are protected by transplantation of new cells into the brain or injection of a neurotrophic factor into the brain. Although the majority of these regenerative therapies are still under study, some are already being applied clinically, and thus are receiving attention as new therapeutic treatments for various brain diseases. For example, Non-Patent Documents 1 and 2 disclose a therapeutic treatment for introducing a neurotrophic factor into the brain, by transplanting cells producing a neurotrophic factor into the brain to compensate for deficient amounts of the neurotrophic factor.

Non-Patent Document 1: "Regenerative Treatments of the Brain (Nou-no-saisei-iryou)," (online), Japan Neurosurgical Society, http://square.umin.ac.jp/neuroinf/patient/701.html (accessed Oct. 16, 2006); and Non-Patent Document 2: "Perspective on Neuroprotective and Neural Repairing Agents (Shinkei-hogo, shinkei-shuhukuyaku-no-tenbou)," (online), http://www.h2.dion.ne.jp/~park/index1/i1014hogo.html (accessed Oct. 16, 2006).

DISCLOSURE OF THE INVENTION

Problem(s) to be Solved by the Invention

Incidentally, since a neurotrophic factor having a function of repairing the abovementioned central nervous system cells cannot pass through the blood-brain barrier (i.e., the barrier between the brain and blood vessels for preventing the entry of a harmful substance into the brain), the neurotrophic factor cannot be administered into the brain via an intravenous injection, and the like. Consequently, the only conventional regenerative therapies of the brain were either the abovementioned method of transplanting cells producing the neurotrophic factor into the brain, or the method of directly injecting the neurotrophic factor into the brain.

However, since a procedure for the injection of the neurotrophic factor or the transplantation of cells to the brain also presents considerable risks, such as damage to the central nervous system cells and the introduction of infections into the brain, the treatment method can only be achieved at specific advanced medical facilities, and thus in spite of fact that the number of patients is increasing, patients have been unable to easily receive a treatment anywhere.

Thus, the present invention was achieved in view of the abovementioned problems, and as such, aims to provide a novel and improved neurotrophic factor production promoting device, which is able to promote the production of the neurotrophic factor or neurotrophic factor-like substance in an affected area by a simple technique that, regardless of the place of treatment, can be performed without the transplantation of cells or the injection into the affected area, in order to prevent or treat various diseases such as brain diseases.

Means for Solving the Problem(s)

Although the mechanism of the effects of a magnetic treatment for brain diseases has not been completely elucidated, after thorough research by the present inventors, it was found that applying a high frequency alternating magnetic field of a predetermined frequency to specific cells (cells that are capable of producing the neurotrophic factor or neurotrophic factor-like substance, e.g., glial cells) of an affected area of a subject to be treated at an appropriate magnetic field intensity (e.g., no more than 0.01 Tesla) allows the concentration of calcium ions ($Ca^{2+}$) within these cells to be increased so that an exocytotic reaction of the neurotrophic factor and/or neurotrophic factor-like substance (hereinafter, "the neurotrophic factor and/or neurotrophic factor-like substance" may also be referred to as, "neurotrophic factor group") is induced, and allows messenger ribonucleic acid (mRNA) to be increased in the cells so that the synthesis and release of the neurotrophic factor group is promoted, thereby allowing the production of the neurotrophic factor group to be promoted.

Thus, the present inventors focused on the neurotrophic factor group production promoting effect in such cells, and therefore, thoroughly researched a frequency of a high frequency alternating magnetic field to be applied on cells by conducting various experiments and studies. As a result, a frequency of a suitable high frequency alternating magnetic field capable of significantly enhancing the magnetic treatment effect of promoting the production of neurotrophic factor group has been found, to thereby allow the below-mentioned invention of the present application to be achieved.

In order to solve the abovementioned problems, from a perspective of the present invention, a neurotrophic factor production promoting device is provided for promoting the production of the neurotrophic factor or the neurotrophic factor-like substance via application of magnetic stimulation to cells. This neurotrophic factor production promoting device includes a high frequency electromagnetic wave generating means generating a high frequency electromagnetic wave of a high frequency for promotion of production selected from the range of 20 MHz to 180 MHz, 280 MHz to 600 MHz, or 700 MHz to 1000 MHz, in order to apply a high frequency alternating magnetic field of the high frequency for the promotion of production to the cells at a magnetic flux density of no more than 0.01 Tesla, whereby the magnetic stimulation by the high frequency alternating magnetic field of the high frequency for the promotion of production allows the concentration of calcium ions ($Ca^{2+}$) within the cells to be increased so that the exocytosis of the neurotrophic factor or the neurotrophic factor-like substance is induced, and the magnetic stimulation allows the messenger ribonucleic acid (mRNA) of the neurotrophic factor or the neurotrophic factor-like substance to be increased in the cells so that the synthesis and the extracellular release of the neurotrophic factor or the neurotrophic factor-like substance are promoted.

By generating a high frequency electromagnetic wave of the high frequency for the promotion of production that is suitable for magnetic treatment via the above structure, it allows the abovementioned high frequency alternating magnetic field of the high frequency for the promotion of production to be emitted, and to be applied to cells such as those of the affected area of a subject to be treated. The production of the neurotrophic factor or the neurotrophic factor-like substance in cells in an affected area of a subject to be treated is promoted via this magnetic stimulation, to thereby allow cells that have been weakened, damaged, or reduced in number by a disease to be regenerated by the neurotrophic factor or the neurotrophic factor-like substance, and allow the abovementioned disease to be treated by a suitable magnetic treatment. Such a magnetic treatment allows to easily treat or prevent a disease, without the transplantation of cells or the injection to the affected area, regardless of the place of treatment.

Moreover, applying magnetic stimulation to cells capable of producing the neurotrophic factor group via the abovementioned high frequency alternating magnetic field within the range of 20 MHz to 180 MHz, 280 MHz to 600 MHz, or 700 MHz to 1000 MHz allows for, for example, at least a 2-fold increase in the neurite outgrowth of cells that have been weakened and the like by a disease, when compared with an unstimulated group, which thereby allows the magnetic treatment effect to be enhanced.

In addition, the abovementioned cells that are capable of producing the neurotrophic factor and/or neurotrophic factor-like substance may also include a glial cell, a neurocyte, a fibroblast, a vascular endothelial cell, an epidermal cell, a keratinocyte, an immunocyte, or a muscle cell.

Moreover, the abovementioned neurotrophic factor may also include at least one selected from a nerve growth factor (NGF), a brain-derived neurotrophic factor (BDNF), a basic fibroblast growth factor-2 (FGF-2), and a glial cell-line derived neurotrophic factor (GDNF).

Furthermore, the neurotrophic factor-like substance may also include at least one selected from adenosine, adenosine monophosphate (AMP), a manganese ion, genipin, lysophosphatidylethanolamine, ganglioside, and Rho-kinase.

In addition, the abovementioned neurotrophic factor production promoting device may also be a treatment device employed to treat a disease caused by a weakening of, damage to, or a reduction in the number of the central nervous system cells or cerebrospinal nervous system cells.

Furthermore, the abovementioned disease may also be at least one selected from a neurodegenerative disorder, depression, a cerebrovascular disease, and a spinal cord injury.

Moreover, the abovementioned high frequency for the promotion of production may be selected from the range of 60 MHz to 180 MHz, 280 MHz to 300 MHz, 450 MHz to 550 MHz, or 900 MHz to 950 MHz. Accordingly, since this allows for, for example, at least a 2.5-fold increase in the neurite outgrowth of the abovementioned cells weakened and the like by a disease, when compared with an unstimulated group, it is able to further enhance the magnetic treatment effect thereof.

In addition, the abovementioned high frequency for the promotion of production may be selected from the range of 100 MHz to 160 MHz. Accordingly, since this allows for, for example, at least a 3.0-fold increase in the neurite outgrowth of the abovementioned cells weakened and the like by a disease, when compared with an unstimulated group, it is able to even further enhance the magnetic treatment effect thereof.

Furthermore, the abovementioned high frequency for the promotion of production may be selected from the range of 120 MHz to 160 MHz. Accordingly, since this allows for, for example, at least a 3.5-fold increase in the neurite outgrowth of the abovementioned cells weakened and the like by a disease, when compared with an unstimulated group, it is able to remarkably enhance the magnetic treatment effect.

Moreover, the abovementioned high frequency electromagnetic wave generating means may also include a high frequency oscillation means outputting a high frequency electric current, and a high frequency antenna generating the high frequency electromagnetic wave of the high frequency for the promotion of production via the application of the high frequency electric current from the high frequency oscillation means. Accordingly, this allows the high frequency electromagnetic wave of the high frequency for the promotion of production to be suitably generated, so that the high frequency alternating magnetic field of the high frequency for the promotion of production can be appropriately applied to the cells of the affected area of the subject to be treated.

In addition, the abovementioned high frequency electromagnetic wave generating means may also intermittently generate the high frequency electromagnetic wave, by repeating an on time period in which the high frequency electromagnetic wave is generated and an off time period in which the high frequency electromagnetic wave is not generated, at a predetermined cycle. Accordingly, since this allows the high frequency alternating magnetic field to be intermittently generated and applied to the cells of the affected area of the subject to be treated, it is possible to repeatedly switch between a state in which the high frequency alternating magnetic field is applied to these cells and a state in which it is not applied to these cells. Thus, changes in the high frequency alternating magnetic field stimulation applied to the cells occur, so as to allow the magnetic treatment effect to be enhanced.

Furthermore, the abovementioned high frequency electromagnetic wave generating means may also intermittently generate the high frequency electromagnetic wave, by repeating a first on time period in which the high frequency electromagnetic wave is generated and a first off time period in which the high frequency electromagnetic wave is not generated, at a cycle corresponding to 2.0±10% kHz. In addition, the abovementioned high frequency electromagnetic wave generating means may also intermittently generate the high frequency electromagnetic wave, by repeating a second on time period in which the high frequency electromagnetic wave is generated and a second off time period in which the high frequency electromagnetic wave is not generated, at a cycle corresponding to 7.8±10% Hz. Accordingly, the high frequency alternating magnetic field is intermittently generated, at a suitable time interval that the cells of the affected area of the subject to be treated are responsive to, to be applied to the cells of the affected area.

Moreover, a low frequency electromagnetic wave generating means generating a low frequency electromagnetic wave of a low frequency for the promotion of production selected from the abovementioned range of 2.0±10% kHz may also be included, in order to apply a low frequency alternating magnetic field of the low frequency for the promotion of production to the cells. Accordingly, this allows not only the abovementioned high frequency alternating magnetic field to be applied to the cells of the affected area of the subject to be treated, but also the low frequency alternating magnetic field of the low frequency for the promotion of production suitable for magnetic treatment to be applied thereto, so that the magnetic treatment effect can be further enhanced.

In addition, the abovementioned low frequency electromagnetic wave generating means may also include a low frequency oscillation means outputting a low frequency electric current, and a low frequency antenna generating the low frequency electromagnetic wave of the low frequency for the promotion of production via the application of the low frequency electric current from the low frequency oscillation means. Accordingly, this allows the low frequency electromagnetic wave of the low frequency for the promotion of production to be suitably generated, so that the low frequency alternating magnetic field of the low frequency for the promotion of production can be appropriately applied to the cells of the affected area of the subject to be treated.

Furthermore, a rise time of the low frequency electric current applied to the abovementioned low frequency antenna may be no more than 0.1 µsec. Accordingly, since this allows a rate of change in an intensity of the low frequency alternating magnetic field to be increased, the cells become more sensitized to the low frequency magnetic field.

Moreover, the abovementioned low frequency electromagnetic wave generating means may also intermittently generate the low frequency electromagnetic wave, by repeating an on time period in which the low frequency electromagnetic wave is generated and an off time period in which the low frequency electromagnetic wave is not generated, at a predetermined cycle. Accordingly, since this allows the low frequency alternating magnetic field to be intermittently generated and applied to the cells of the affected area of the subject to be treated, it is possible to repeatedly switch between a state in which the low frequency alternating magnetic field is applied to these cells and a state in which it is not applied to these cells. Thus, changes in the low frequency alternating magnetic field stimulation applied to the cells occur, so as to allow the magnetic treatment effect to be enhanced.

In addition, the abovementioned low frequency electromagnetic wave generating means may also intermittently generate the low frequency electromagnetic wave, by repeating a third on time period in which the low frequency electromagnetic wave is generated and a third off time period in which the low frequency electromagnetic wave is not generated, at a cycle corresponding to 7.8±10% Hz. Accordingly, the low frequency alternating magnetic field is intermittently generated, at a suitable time interval that the cells of the affected area of the subject to be treated are responsive to, to be applied to the cells.

Furthermore, the abovementioned high frequency electromagnetic wave generating means may also intermittently generate the high frequency electromagnetic wave, by repeating an on time period in which the high frequency electromagnetic wave is generated and an off time period in which the high frequency electromagnetic wave is not generated, at a predetermined cycle, and the on time period of the high frequency electromagnetic wave and the on time period of the low frequency electromagnetic wave may be synchronized with each other. Accordingly, since the high frequency alternating magnetic field and the low frequency alternating magnetic field are repeatedly generated/not generated with the same timing, a time when both alternating magnetic fields are applied to the cells of the affected area and a time when both alternating magnetic fields are not applied to the cells of an affected area can be clearly separated. Thus, changes in the alternating magnetic field stimulation applied to these cells occur, so as to allow the magnetic treatment effect to be enhanced.

Moreover, the abovementioned high frequency electromagnetic wave generating means may also generate the high frequency electromagnetic wave of the high frequency for the promotion of production, by intermittently generating a high frequency electromagnetic wave of a frequency higher than the high frequency for the promotion of production, at a cycle corresponding to the high frequency for the promotion of production. Accordingly, by employing the high frequency electromagnetic wave of the high frequency as a carrier wave, the abovementioned high frequency electromagnetic wave of the high frequency for the promotion of production can be generated.

In addition, the high frequency electromagnetic wave of the high frequency for the promotion of production generated by the abovementioned high frequency electromagnetic wave generating means may also include a higher harmonic wave occurring when a high frequency electromagnetic wave of less than the high frequency for the promotion of production is generated. Specifically, the high frequency electromagnetic wave generating means may also include an electromagnetic wave generating means additionally generating the high frequency electromagnetic wave of the high frequency for the promotion of production as a higher harmonic wave, when generating an electromagnetic wave of a frequency that is an integer sub-multiple of the abovementioned high frequency for the promotion of production.

Effects of the Invention

According to the present invention described above, the production of the neurotrophic factor or neurotrophic factor-like substance in an affected area is promoted by a simple magnetic treatment, so that prevention or treatment of various diseases such as brain diseases can be performed, regardless of the place of treatment, and without the transplantation of cells or the injection into the affected area.

BRIEF DESCRIPTION OF THE DRAWINGS

FIG. 2B is a plan view showing an oscillation coil, and a plan view showing another example of the internal structure of the magnetic treatment device of the same embodiment;

FIG. 3 is a block diagram showing an example of a circuit structure of the magnetic treatment device of the same embodiment;

FIG. 5A is an explanatory view showing a treatment aspect in which the magnetic treatment device of the same embodiment is employed;

FIG. 5B is an explanatory view showing a treatment aspect in which the magnetic treatment device of the same embodiment is employed;

FIG. 7 is a perspective view showing a structure of a magnetic stimulation device employed in Experiment 1 of an Example of the present invention;

FIG. 8 is a graph showing experimental results of Experiment 1 of an Example of the present invention;

FIG. 9 is a graph showing experimental results of Experiment 2 of an Example of the present invention;

FIG. 10 is a graph showing experimental results of Experiment 5 of an Example of the present invention; and FIG. 11 is a graph showing measurement results of a frequency of an electromagnetic wave generated by the magnetic treatment device of the abovementioned embodiment.

Figure 1:
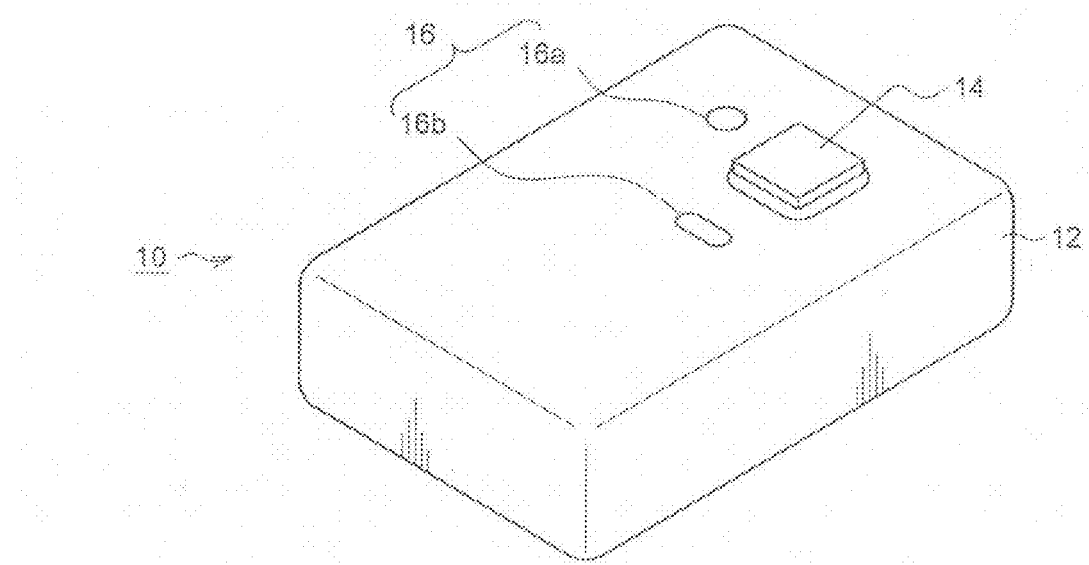
FIG. 1 is a perspective view showing an exterior of a magnetic treatment device of a first embodiment of the present invention.

EXPLANATION OF THE REFERENCE NUMERALS 10, 10A, 10B Magnetic treatment device (Neurotrophic factor production promoting device)
12 Housing
16 Display portion
18 Power source portion
20 Control block
21 Power source supply circuit
22 Main control circuit
23 Clock generating circuit
24 High frequency wave oscillation means
25 Low frequency wave oscillation means
30, 30A, 30B High frequency coil
40, 40A, 40B Low frequency coil
50 Oscillation coil

BEST MODE FOR CARRYING OUT THE INVENTION

Hereinafter, the details of preferred embodiments of the present invention will be explained with reference to the appended drawings. Moreover, with regard to the specification and drawings of the present application, the constituent elements having a substantially similar functional structure have been given the same reference numeral to omit a duplicate description thereof.

First Embodiment

Hereinafter, a magnetic treatment device will be described as an example of a neurotrophic factor production promoting device of a first embodiment of the present invention. The magnetic treatment device promotes the production of the neurotrophic factor and/or the neurotrophic factor-like substance (hereinafter "the neurotrophic factor and/or neurotrophic factor-like substance" will be referred to as a "neurotrophic factor group") in cells by applying magnetic stimulation to the cells of an affected area of a human body, in order to prevent and treat various diseases such as a brain diseases.
Structure of the Treatment Device First, an external structure of a magnetic treatment device 10 of the present embodiment will be explained with reference to FIG. 1. Moreover, FIG. 1 is a perspective view showing the external structure of the magnetic treatment device 10 of the present embodiment.

As shown in FIG. 1, the magnetic treatment device 10 includes, for example, a housing 12, an operating portion 14, and a display portion 16.

The housing 12 is a case for internally storing each main apparatus of the magnetic treatment device 10, that is formed of a synthetic resin, such as a plastic and the like. This housing 12 includes a flat substantially rectangular parallel-piped shape (e.g., approximately 8 cm length×6 cm width×2 cm height). However, the shape thereof is not specifically limited to that of the above example. For example, the shape thereof can be modified into an arbitrary shape, such as a substantially spherical shape, a substantially oval shape, a substantially rod shape, a substantially cube shape, any other shape that is easily grasped by a user, or the like. The user of the magnetic treatment device 10 grasps the housing 12, and an electromagnetic wave (including an alternating magnetic field) emitted from the magnetic treatment device 10 can be applied to the affected area, by bringing the magnetic treatment device 10 into immediate contact with the affected area or into a proximity that is within a predetermined distance with respect to the affected area.

The operation portion 14 is a switch and the like, for turning the magnetic treatment device 10 on or off (e.g., for irradiating the alternating magnetic field). For example, the user can switch the magnetic treatment device 10 between an activated or deactivated mode by pressing the operation portion 14 each time.

Moreover, the display portion 16 is composed of a light-emitting lamp, such as a light-emitting diode (LED), and the like. This display portion 16 may display the activated or deactivated mode of the magnetic treatment device 10, or a state of remaining power, or a state of electric charge of the below-mentioned power source portion (not shown), or the like. In the present embodiment, this display portion 16 is composed of two LEDs: a red LED 16a and a green LED 16b. This red LED 16a lights up when the remaining power of the battery and the like of the power source portion is above a predetermined level, and flashes when the remaining power of the battery is below this level, for example. Moreover, the green LED 16b lights up or flashes when the magnetic treatment device is activated, and turns off when the magnetic treatment device is deactivated.

However, the display portion 16 is not specifically limited to the above example. For example, the display portion 16 may also be composed of a liquid crystal display device (LCD) that is capable of displaying characters or graphics and the like. Accordingly, the display portion 16 is capable of displaying a variety of information, such as information regarding the intensity or frequency of the electromagnetic wave (alternating magnetic field) irradiated by the magnetic treatment device 10, time period that the irradiation is sustained, irradiation timing, treatment schedule, amount of battery remaining, time of day, and temperature.

Next, the internal structure of the magnetic treatment device 10 of the present embodiment will be explained with reference to FIGS. 2A and 2B. Moreover, FIG. 2A is a plan view showing an example of the internal structure of the magnetic treatment device 10 of the present embodiment (magnetic treatment device 10A); and FIG. 2B is plan view showing another example of the internal structure of the magnetic treatment device 10 of the present embodiment (magnetic treatment device 10B), and a perspective view showing an oscillation coil 50 within.

Figure 2A:
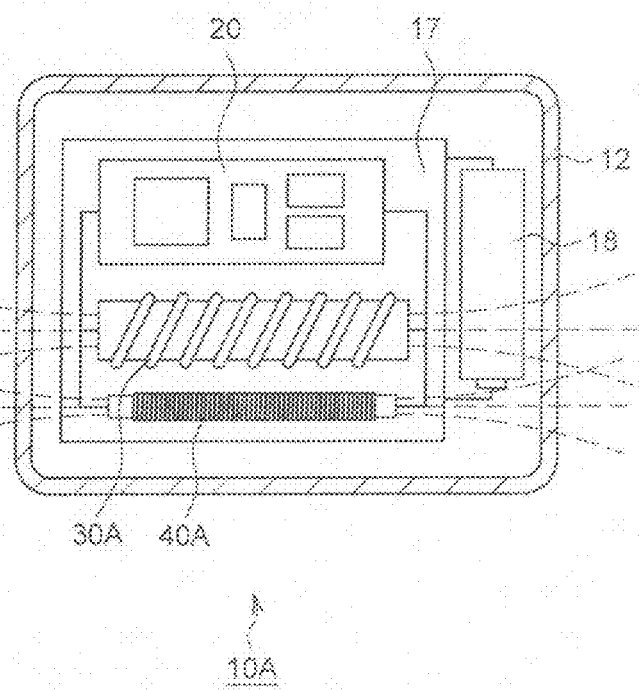
FIG. 2A is a plan view showing an example of an internal structure of the magnetic treatment device of the same embodiment.

As shown in FIG. 2A, for example, a power source portion 18, a control block 20, a high frequency coil 30A, and a low frequency coil 40A are provided within the housing 12 of the magnetic treatment device 10A. Among these, the control block 20, the high frequency coil 30A, and the low frequency coil 40A, for example, are mounted on a same substrate 17, and are collectively attachable to/detachable from the housing 12.

The power source portion 18 is a direct current power source device composed of a battery (e.g., 9V dry battery), such as various types of rechargeable batteries and dry batteries, which supplies electric power to each portion of the magnetic treatment device 10A. Moreover, the control block 20 which is a circuit board equipped with a control device controlling each portion in the magnetic treatment device 10A, a high frequency oscillation circuit oscillating a high frequency wave, a clock generating circuit, and the like (none is shown) will be described in detail hereinafter (see FIG. 3).

The high frequency coil 30A is an example of an antenna (high frequency antenna) emitting a high frequency electromagnetic wave by being applied a high frequency electric current. This high frequency coil 30A is a loop antenna composed of a coil having eight turns of a comparatively thick copper wire, for example. The above high frequency coil 30A is, for example, capable of generating a high frequency electromagnetic wave that is a high frequency for the promotion of production (e.g., 100 MHz to 160 MHz) by being applied the high frequency electric current from the abovementioned control block 20, and emitting it peripherally. This high frequency electromagnetic wave includes a high frequency alternating magnetic field and a high frequency alternating electric field.

On the other hand, the low frequency coil 40A is an example of an antenna (low frequency antenna) emitting a low frequency electromagnetic wave by being applied a low frequency electric current. This low frequency coil 40A is, for example, a loop antenna composed of a coil having 500 turns of a comparatively thin copper wire on a shaft core. The above low frequency coil 40A is, for example, capable of generating a low frequency electromagnetic wave, which is at a frequency of approximately 2.0 kHz, by being applied the low frequency electric current from the abovementioned control block 20, and emitting it peripherally. This low frequency electromagnetic wave includes a low frequency alternating magnetic field and a low frequency alternating electric field.

The high frequency coil 30A and the low frequency coil 40A are mounted in parallel, for example, so as to have the central shafts thereof in, for example, substantially the same direction. Also, the central shafts of the high frequency coil 30A and the low frequency coil 40A are disposed so as to be parallel to the widest surface (upper and lower surfaces of FIG. 1) of the housing 12. Thus, the high frequency alternating magnetic field and the low frequency alternating magnetic field are formed so as to have a line of magnetic force perpendicular to a side surface of the housing 12, via the high frequency electromagnetic wave and the low frequency electromagnetic wave generated by the high frequency coil 30A and the low frequency coil 40A.

Next, the magnetic treatment device 10B shown in FIG. 2B will be described. As shown in FIG. 2B, for example, a power source portion 18, a control block 20, and an oscillation coil 50 including a high frequency coil 30B and a low frequency coil 40B are provided within the housing 12 of the magnetic treatment device 10B. Among these, the control block 20, the high frequency coil 30B, and the low frequency coil 40B, for example, are mounted on a same substrate 17, and are collectively attachable to/detachable from the housing 12. Moreover, when the magnetic treatment device 10B of FIG. 2B is compared with the abovementioned magnetic treatment device 10A of FIG. 2A, since only the structure and arrangement of the high frequency coil 30B and the low frequency coil 40B are different therefrom, the detailed description of all the other substantially similar constituent elements will be omitted.

As shown in FIG. 2B, the oscillation coil 50 is formed, for example, of the high frequency coil 30B coiled with a comparatively thick copper wire, and the low frequency coil 40B coiled with a comparatively thin conductive wire, on the outer periphery of an acrylic annular base portion 52 having a diameter of 3 cm, an axial width of 9 mm, and a radial thickness of 2 mm. Among these, the high frequency coil 30B is a single turn solenoid coil (diameter of 3 cm); and the low frequency coil 40B is a 200 turn solenoid coil (diameter of 3 cm, and a winding width of 5 mm). In this manner, the oscillation coil 50 is a coil having two kinds of coils, the high frequency coil 30B and the low frequency coil 40B, coaxially formed on a single acrylic annular base portion 52.

This oscillation coil 50 is arranged with the central shafts thereof (of the high frequency coil 30B and the low frequency coil 40B) disposed so as to be perpendicular to the widest surface (upper and lower surfaces of FIG. 1) of the housing 12. Thus, the high frequency alternating magnetic field and the low frequency alternating magnetic field are formed so as to have a line of magnetic force perpendicular to the widest surface of the housing 12, via the high frequency electromagnetic wave and the low frequency electromagnetic wave generated by the high frequency coil 30B and the low frequency coil 40B.

As mentioned above, the two structural examples (10A and 10B) of the magnetic treatment device 10 were described with reference to FIGS. 2A and 2B. The abovementioned magnetic treatment device 10A and the magnetic treatment device 10B differ in their shape and a direction that the lines of magnetic force of the alternating magnetic fields are formed. However, in either case, the high frequency electromagnetic wave and the low frequency electromagnetic wave generated by the high frequency coil 30A, 30B (hereinafter collectively referred to as "high frequency coil 30") and by the low frequency coil 40A, 40B (hereinafter collectively referred to as "low frequency coil 40") are irradiated, for example, so as to be substantially uniformly dispersed in all circumferential directions with the central shaft of the coil as a center thereof. Thus, the magnetic treatment effect is provided regardless of which surface of the magnetic treatment device 10A, 10B is in direct contact with or in the proximity of the affected area at which angle. Accordingly, treatment using the magnetic treatment device 10 becomes easy.

Furthermore, the antenna emitting the high frequency electromagnetic wave or the low frequency electromagnetic wave is not specifically limited to the abovementioned examples of loop antenna such as the high frequency coil 30 and the low frequency coil 40 of FIG. 2. For example, various types of antennas, such as rod antenna and the like, may be employed.

Next, the structure and operation of the circuit of the magnetic treatment device 10 of the present embodiment will be explained with in detail reference to FIG. 3. Moreover, FIG. 3 is a block diagram showing a circuit structure of the magnetic treatment device 10 of the present embodiment.

Moreover, the below-described control block 20 and the abovementioned high frequency coil 30 are one example of a structure of the high frequency electromagnetic wave generating means generating the high frequency electromagnetic wave of a predetermined frequency for the promotion of production (e.g., 83.3 MHz). In addition, this control block 20 and the abovementioned low frequency coil 40 are one example of the structure of the low frequency electromagnetic wave generating means generating the low frequency electromagnetic wave of a predetermined frequency (e.g., 2 kHz).

As shown in FIG. 3, the control block 20 includes, for example, a main control circuit 22, a power source supply circuit 21, a clock generating circuit 23, a high frequency oscillation means 24, and a low frequency oscillation means 25.

The main control circuit 22 is composed, for example, of a one-chip microcomputer, and functions to control each portion within the control block 20.

The power source supply circuit 21 includes, for example, an on/off control circuit 212, a booster circuit 214, and a step-down circuit 216, and functions to control the supply of electric power from the abovementioned power source portion 18 to each portion within the control block 20. Specifically, the on/off control circuit 212, for example, detects the on/off of the switch of the operation portion 14, and inputs the detection results into the main control circuit 22. In addition, the on/off control circuit 212 turns the electric power supply from the power source portion 18 to the high frequency coil 30 and the low frequency coil 40, and the like, on or off, based on an on/off instruction from the main control circuit 22.

Moreover, the booster circuit 214, for example, is capable of boosting the electric power from the power source portion 18 that is composed of a 9V dry battery, when necessary. Accordingly, the voltage supplied to the high frequency coil 30 and the low frequency coil 40 can be maintained at 9V, for example. Furthermore, the booster circuit 214, for example, can also output a battery consumption error signal to the main control circuit 22 when the voltage that can be output therefrom falls below a predetermined level as a result of the battery consumption of the power source portion 18, and the like. As a result, when the error signal is input, the main control circuit 22, for example, controls the switching from lightning to flashing of the red LED 16a, so that the user can be notified of the battery consumption.

In addition, the step-down circuit 216 is capable of maintaining the voltage supplied to the main control circuit 22 and the like at 5V, for example, via a step down in the power of the power source portion 18. Moreover, the step-down circuit 216, for example, can also output a voltage reduction error signal to the main control circuit 22 when the voltage that can be output therefrom falls below a predetermined level, as a result of the battery consumption of the power source portion 18, and the like. As result thereof, the main control circuit 22 controls the overall operation of the magnetic treatment device 10 so as to prevent trouble, such as an unexpected stoppage in operation occurring from a reduction in voltage, and the like, for example. As a result, since the green LED 16b, which is lighted during the operation of the magnetic treatment device 10, is controlled to be turned off, the user can be notified when the operation of the magnetic treatment device 10 is stopped.

The clock generating circuit 23, for example, generates a clock signal at a predetermined frequency, which is output to the main control circuit 22. This clock generating circuit 23, for example, is constructed so as to be capable of generating a 32.7 kHz clock signal and a 10 MHz clock signal. The main control circuit 22 outputs a clock signal inputted from this clock generating circuit 23 to the low frequency oscillation circuit 254. The low frequency oscillation circuit 254, for example, generates a 2.0 kHz clock signal and a 7.81 Hz clock signal based on the above clock signal, and outputs these to a modulation circuit 246 and a coil drive circuit 258, respectively.

The high frequency oscillation means 24 generates a high frequency electric current (e.g., approximately 83.3 MHz) of a predetermined frequency for the promotion of production, which is applied to the high frequency coil 30. This high frequency oscillation means 24 includes, for example, a frequency control circuit 242, a high frequency oscillation circuit 244, the modulation circuit 246, and a coil drive circuit 248.

The frequency control circuit 242 functions to control the frequency of the high frequency wave generated by the high frequency oscillation circuit 244. Specifically, this frequency control circuit 242, for example, controls the frequency of the high frequency wave outputted by the high frequency oscillation circuit 244, based on the high frequency wave fed back from the high frequency oscillation circuit 244, and a frequency setting signal from the main control circuit 22. As a result, the high frequency oscillation circuit 244 stably oscillates a high frequency wave of 83.3 MHz, for example, which is capable of being output to the modulation circuit 246. Moreover, so long as the high frequency wave is a signal that is capable of transmitting a predetermined frequency, it may be either a high frequency electric current or high frequency voltage. In addition, the high frequency wave of 83.3 MHz outputted by the abovementioned high frequency oscillation circuit 244 is a substantially sinusoidal wave signal, for example.

The modulation circuit 246, for example, is capable of intermittently outputting the high frequency wave of 83.3 MHz outputted from the high frequency oscillation circuit 244, based on the clock signal inputted from the low frequency oscillation circuit 254, with a two-step on/off process, for example.

The first step of the on/off process, for example, is a process of partially cutting and intermittently outputting the high frequency wave of 83.3 MHz inputted based on the 2.0 kHz clock signal. Specifically, the modulation circuit 246, for example, repeats a process in which, during a predetermined first on time period (e.g., 400 μsec), the high frequency wave of 83.3 MHz is output as is, and then, during a predetermined first off time period (e.g., 100 μsec), it is output as a signal in which an amplitude of the abovementioned high frequency wave is cut. Accordingly, the modulation circuit 246, for example, is capable of turning on/off the 83.3 MHz high frequency wave inputted as a constant sinusoidal wave at, for example, a cycle equivalent to 2.0 kHz, so as to intermittently oscillate the 83.3 MHz high frequency wave. In other words, the modulation circuit 246, for example, is able to perform a modulation process in which a signal showing a substantially rectangular wave of 2.0 kHz is output, with the 83.3 MHz high frequency wave inputted from the high frequency oscillation circuit 244 as a carrier wave.

Furthermore, the second step of the on/off process is one in which, for example, the high frequency wave formed by the abovementioned first step of the on/off process is further partially cut and intermittently output, based on the 7.81 Hz clock signal. Specifically, the modulation circuit 246, for example, repeats a process in which, during a predetermined second on time period (e.g., 64 msec), the high frequency wave is output as is, and then, during the predetermined second off time period (e.g., 64 msec), it is output as a signal in which the amplitude of the abovementioned high frequency wave is cut. Accordingly, the modulation circuit 246, for example, turns on/off, at a cycle equivalent to 7.81 Hz, the 83.3 MHz high frequency wave that is intermittent at a cycle equivalent to 2.0 kHz described above, and is able to intermittently oscillate a high frequency wave that is intermittent at an even larger cycle. In other words, the modulation circuit 246, for example, is able to output a signal showing a substantially rectangular wave of 7.81 Hz, with the 83.3 MHz high frequency wave inputted from the high frequency oscillation circuit 244 as a carrier wave.

The high frequency wave formed by the two-step on/off process via this modulation circuit 246 is input to the coil drive circuit 248. The coil drive circuit 248 amplifies the inputted high frequency wave with the electric power from the power source supply circuit 21, intermittently oscillates the high frequency electric current with a frequency of 83.3 MHz at the two cycles equivalent to 2.0 kHz and 7.81 Hz, and applies it to the high frequency coil 30. At such a time, the coil drive circuit 248 controls a magnetic field intensity (magnetic flux density) of the high frequency electromagnetic wave generated by the high frequency coil 30, by controlling the electric current value of the high frequency electric current applied to the high frequency coil 30, so that the magnetic field intensity of the high frequency alternating magnetic field applied to the affected area is within the range of 50 nT to 0.01 T, for example. For example, when measuring the magnetic field intensity of the high frequency electromagnetic wave generated by the high frequency coil 30B of the magnetic treatment device 10B of the present embodiment, the magnetic field intensity was 1.3 µT, thus enabling a high frequency alternating magnetic field of no less than 50 µT to be applied to the affected area, within an effective distance of 3 mm from the high frequency coil 30B.

On the other hand, the low frequency oscillation means 25, for example, generates a low frequency electric current of approximately 2 kHz, which is applied to the low frequency coil 40. This low frequency oscillation means 25, for example, includes the low frequency oscillation circuit 254, and the coil drive circuit 258.

As mentioned above, the low frequency oscillation circuit 254 generates, for example, a 2.0 kHz clock signal and a 7.81 Hz clock signal, based on the clock signal inputted from the main control circuit 22, which are output to the modulation circuit 246 and the coil drive circuit 258, respectively. Moreover, the low frequency oscillation circuit 254, for example, generates the 2.0 kHz low frequency wave as a substantially rectangular wave based on the above clock signal, and then, by implementing an on/off process (every 64 msec) at a cycle that is equivalent to approximately 7.81 Hz on this low frequency, for example, to generate the 2.0 kHz low frequency wave that is intermittent at a cycle equivalent to approximately 7.81 Hz. Specifically, the low frequency oscillation circuit 254, for example, repeats a process in which, during a predetermined third on time period (e.g., 64 msec), the low frequency wave is output as is, and then, during a predetermined third off time period (e.g., 64 msec), it is output as a signal in which the amplitude of the abovementioned low frequency wave is cut. Accordingly, the low frequency oscillation circuit 254, for example, can intermittently oscillate the 2.0 kHz low frequency wave at an on/off cycle equivalent to 7.81 Hz. In addition, a circuit equivalent to the abovementioned frequency control circuit 242 and the modulation circuit 246 may also be provided in front of or behind this low frequency oscillation circuit 254.

The coil drive circuit 258 amplifies the low frequency wave inputted from the low frequency oscillation circuit 254 with electric power from the power source supply circuit 21, intermittently oscillates a high frequency electric current with a frequency of 2.0 kHz at a cycle equivalent to 7.81 Hz, so as to be applied to the low frequency coil 40. At such a time, the coil drive circuit 258 controls the magnetic field intensity (magnetic flux density) of the low frequency electromagnetic wave generated by the low frequency coil 40, by controlling the electric current value of the low frequency electric current applied to the low frequency coil 40, so that the magnetic field intensity of the low frequency alternating magnetic field applied to the affected area is within the range, for example, of 50 nT to 0.01 T. For example, when measuring the magnetic field intensity of the high frequency electromagnetic wave generated by the low frequency coil 40B of the magnetic treatment device 10B of the present embodiment, the magnetic field intensity was 13 µT, thus enabling the low frequency alternating magnetic field of no less than 50 µT to be applied to the affected area, within an effective distance of 3 mm from the low frequency coil 40B.

Electromagnetic Wave Generation Timing

Hereinafter, waveforms of the high frequency electric current and the low frequency electric current applied to the high frequency coil 30 and the low frequency coil 40 of the present embodiment will be described with reference to FIG. 4.

Figure 4:
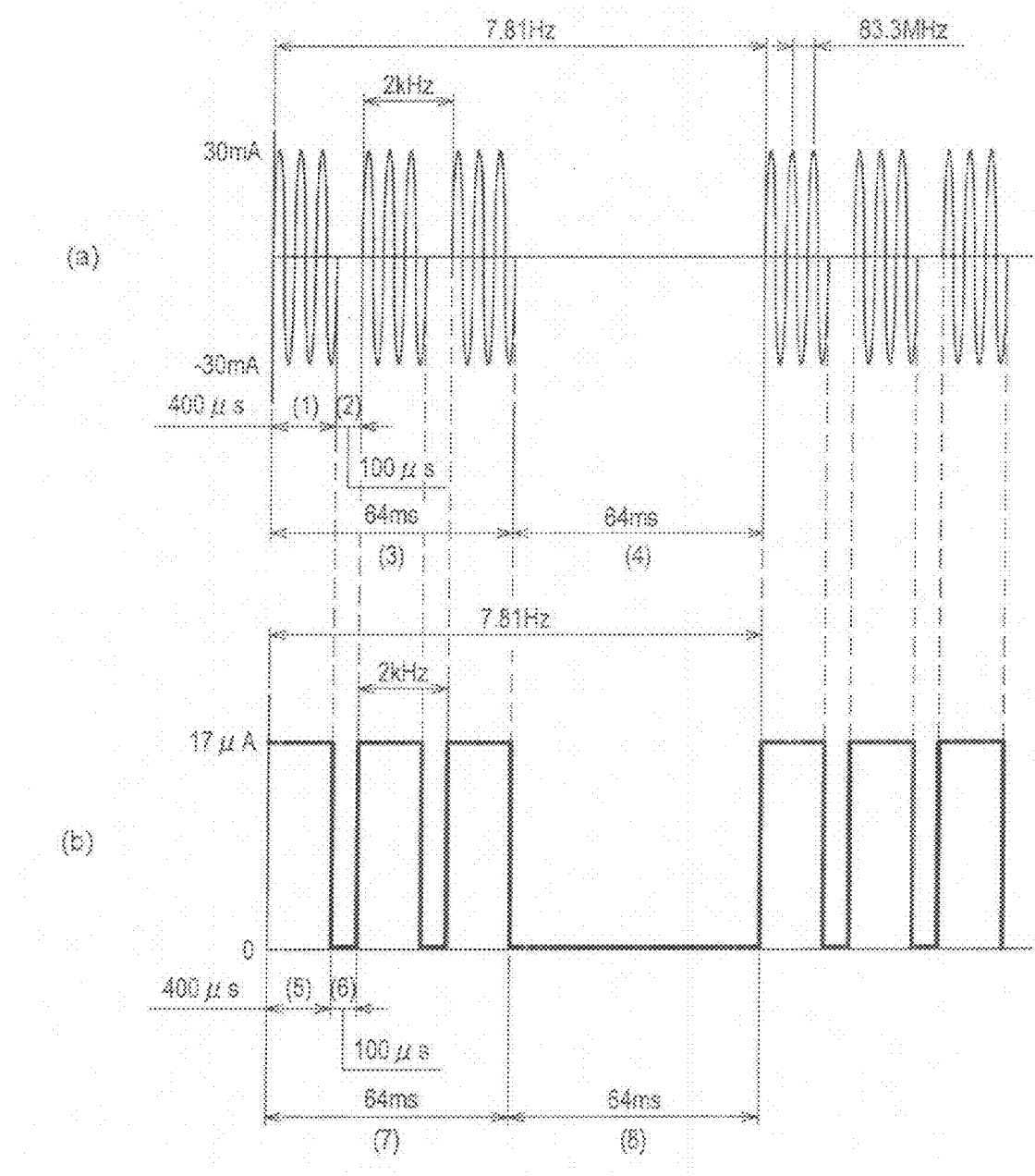
FIG. 4 is a waveform diagram showing waveforms of a high frequency electric current and a low frequency electric current applied to a high frequency coil and a low frequency coil of the same embodiment.

Moreover, FIG. 4 is a waveform diagram showing the waveforms of the high frequency electric current and the low frequency electric current applied to the high frequency coil 30 and the low frequency coil 40 of the present embodiment.

As shown in FIG. 4(*a*), the high frequency electric current of the frequency for the production of promotion (e.g., approximately 83.3 MHz) is applied to the high frequency coil 30. This high frequency electric current has, for example, an amplitude of 30 mA, and forms a symmetrical substantially sinusoidal wave with 0 A as the center thereof.

In addition, this high frequency electric current, for example, forms an interrupted wave that is periodically on/off, rather than a continuous wave. Specifically, the high frequency electric current includes a waveform in which, for example, a 400 µsec first on time period (1), and, for example, a 100 µsec first off time period (2) are alternately repeated, and is intermittent at a cycle corresponding to, for example, approximately 2.0 kHz. Additionally, the above high frequency electric current includes a waveform in which, for example, a 64 msec second on time period (3), and, for example, a 64 msec second off time period (4) are alternately repeated in an even larger time scale, and is also intermittent at a cycle corresponding to, for example, approximately 7.81 Hz. Furthermore, since this high frequency electric current is, for example, an approximately 83.3 MHz high frequency wave, the rise time and fall time thereof are extremely small, for example, no more than 0.003 µsec.

Whereas, as shown in FIG. 4(*b*), the low frequency electric current with a frequency of approximately 2.0 kHz, for example, is applied to the low frequency coil 40. This low frequency electric current, for example, forms a rectangular wave (square wave) that alternates between the two values, 17 µA and 0 A, at a cycle of approximately 2.0 kHz. A time period (5) where this low frequency electric current becomes 17 µA is 400 µsec, for example, and a time period (6) where this low frequency electric current becomes 0 A is 100 µsec, for example. Moreover, the substantially rectangular wave of this low frequency electric current is controlled so as to have a rise time of no more than 0.1 µsec, and a fall time of, for example, no more than 1.0 µsec. In this manner, by significantly shortening the rise time and the fall time of the low frequency electric current applied to the low frequency coil 40 to no more than 0.1 µsec and no more than 1.0 µsec, the amount of change per unit of time in the low frequency electromagnetic wave generated from the low frequency coil 40 via the application of this low frequency electric current can be increased. Thus, since the cells that are the target of magnetic stimulation are more sensitized (i.e., the cells are very susceptible to magnetic stimulation) to an extremely weak magnetic field (e.g., magnetic flux density of 50 nT to 0.01 T), the production of the neurotrophic factor group can be further promoted. Moreover, although the rate of magnetic field change generated in proximity of the coil is not increased even when the rise time of the voltage applied to the low frequency coil 40 is shortened, the rate of magnetic field change can be increased by shortening the rise time of the low frequency electric current as described above, so that the cells are sensitized to the magnetic field.

Furthermore, this low frequency electric current also forms an interrupted wave that is periodically turned on/off at, for example, approximately 7.81 Hz, rather than a continuous wave. Specifically, the low frequency electric current includes a waveform in which, for example, a 64 msec third on time period (6), and, for example, a 64 msec third off time period (8) are alternately repeated, and is intermittent at cycle corresponding to, for example, approximately 7.81 Hz.

Moreover, when comparing FIG. 4(a) and FIG. 4(b), the timing of the high frequency electric current being turned on/off at a cycle of 7.81 Hz and the timing of the low frequency electric current being turned on/off at a cycle of 7.81 Hz are synchronized. More specifically, the high frequency electric current and the low frequency electric current are both intermittent at a cycle corresponding to 7.81 Hz (specifically, for example, repeatedly turned on/off at a cycle of 128 msec). At this time, the timings of application of the high frequency electric current and the low frequency electric current are controlled so that the second on time period of the high frequency electric current (3) (or, the second off time period (4)) and a third on time period of the low frequency electric current (7) (or, the third off time period (8)) have approximately the same timing.

In addition, the time period in which the high frequency electric current is applied to the high frequency coil 30 (1) (on time period of the high frequency electric current), and the time period in which the low frequency electric current is, for example, 17 µA (5) (i.e., time period in which the electric current flows to the low frequency coil 40) are synchronized. More specifically, while the high frequency electric current is intermittent at 2.0 kHz (specifically, for example, repeatedly turned on/off at a cycle of 500 µsec), the low frequency electric current is alternated between the two values, of 17 µA and 0 A, at 2.0 kHz. In this case, the first on time period of the high frequency electric current (1) and the time period in which the low frequency electric current is 17 µA (5) are matched, and the first off time period of the high frequency electric current (2) and the time period in which the low frequency electric current is 0 A (6) are the same. In this manner, the timings of the application of the high frequency electric current and the low frequency electric current are controlled so that the time period in which the high frequency electric current actually flows to the high frequency coil 30 and the time period in which the low frequency electric current actually flows to the low frequency coil 40 are synchronized.

By applying the high frequency electric current described above at, for example, 9V, the high frequency coil 30 is capable of generating and peripherally emitting a high frequency electromagnetic wave with a waveform that is substantially the same, for example, as that of the high frequency electric current shown in FIG. 4(a). This high frequency electromagnetic wave, for example, is a high frequency substantially sinusoidal wave with a frequency of approximately 83.3 MHz, and is periodically intermittent at cycles equivalent to approximately 2.0 kHz and approximately 7.81 Hz. By irradiating the above high frequency electromagnetic wave, for example, a high frequency alternating magnetic field of the high frequency wave for the promotion of production of 83.3 MHz, for example, can be intermittently generated in the periphery of the magnetic treatment device 10.

More specifically, this high frequency alternating magnetic field, for example, has a magnetic flux density (magnetic field intensity) that is periodically increased and decreased at approximately 83.3 MHz, with a maximum amplitude of, for example, 1.3 µT, and is an alternating magnetic field in which the orientation of the magnetic field in both a positive and negative direction periodically fluctuates at approximately 83.3 MHz, and is intermittently generated at cycles that are equivalent to, for example, approximately 2.0 kHz and approximately 7.81 Hz.

By generating the intermittent high frequency alternating magnetic field described above, the magnetic treatment device 10 is not only capable of functioning so as to emit the approximately 83.3 MHz high frequency alternating magnetic field that is the high frequency for the promotion of production to the subject to be treated (e.g., affected area of the human body, and the like), but is also capable of simultaneously irradiating low frequency alternating magnetic fields of approximately 2.0 kHz and approximately 7.81 Hz, with the high frequency alternating magnetic field as a carrier wave.

Moreover, by applying the low frequency electric current described above at, for example, 9V, the low frequency coil 40 is capable of generating and emitting peripherally a low frequency electromagnetic wave with a waveform that is substantially the same, for example, as that of the low frequency electric current shown in FIG. 4(b). This low frequency electromagnetic wave, for example, is a low frequency substantially rectangular wave with a frequency of approximately 2.0 kHz, and is periodically intermittent at approximately 7.81 Hz. By irradiating such a low frequency electromagnetic wave, for example, the low frequency alternating magnetic field of a low frequency for the promotion of production of approximately 2.0 kHz, for example, can be intermittently generated in the periphery of the magnetic treatment device 10.

More specifically, this low frequency alternating magnetic field, for example, has a magnetic field intensity of 13 µT, is an alternating magnetic field occurring by turning on/off at a cycle of 2.0 kHz, a magnetic field with a magnetic field orientation fixed, for example, solely in a positive direction (e.g., repeatedly alternating between a 400 µsec on time period and a 100 µsec off time period), and overall, is intermittently generated at a cycle of approximately 7.81 Hz.

By generating the intermittent low frequency alternating magnetic field described above, the magnetic treatment device 10 is not only capable of functioning so as to emit the approximately 2.0 kHz low frequency alternating magnetic field with the low frequency for the promotion of production on the subject to be treated, but is also capable of simultaneously irradiating a low frequency alternating magnetic field of approximately 7.81 Hz, with this low frequency alternating magnetic field as a carrier wave.

Moreover, applying the abovementioned high frequency electric current and low frequency electric current simultaneously in parallel to the high frequency coil 30 and the low frequency coil 40, allows the above high frequency electromagnetic wave and low frequency electromagnetic wave to be generated simultaneously. As a result, for example, the high frequency alternating magnetic field and the low frequency alternating magnetic field can be simultaneously generated in the periphery of the magnetic treatment device 10. At such a time, as shown by the abovementioned FIG. 4, for example, the intermittent timings, at 7.81 Hz, of the high frequency electromagnetic wave and low frequency electromagnetic wave are mutually synchronized, and the intermittent timing of the 2.0 kHz high frequency electromagnetic wave and the magnetic field generating timing of the 2.0 kHz low frequency electromagnetic wave are synchronized.

Accordingly, the timing for the generation of the high frequency alternating magnetic field by the irradiation of the high frequency electromagnetic wave and the timing for the generation of the magnetic field by the irradiation of the low frequency electromagnetic wave are synchronized. Specifically, while the low frequency coil 40 also generates a magnetic field of a predetermined intensity when the high frequency alternating magnetic field is generated by the high frequency coil 30, the low frequency coil 40 does not also generate a magnetic field at a predetermined level when the high frequency alternating magnetic field is not generated by the high frequency coil 30. On the whole, the magnetic treatment device 10 is consequently capable of periodically repeating the generation/non-generation of the magnetic field (the high frequency alternating magnetic field generated by the high frequency coil 30 and the magnetic field of a predetermined level generated by the low frequency coil 40).

Moreover, although the generation of the alternating magnetic field is described above, the high frequency alternating magnetic field and the low frequency alternating magnetic field are also generated by the irradiation of the abovementioned electromagnetic wave. Since the modes of generation of these alternating magnetic fields, for example, are substantially the same as the mode of generation of the abovementioned alternating magnetic field, the details thereof will be omitted.

Furthermore, although examples that the 83.3 MHz high frequency electromagnetic wave is generated as the high frequency wave for the promotion of production and the 2.0 kHz low frequency electromagnetic wave is generated as the low frequency for the promotion of production are described in the abovementioned FIGS. 3 and 4, the frequency generated is not specifically limited to the above examples. The above magnetic treatment device 10 of the present embodiment is capable of generating a high frequency electromagnetic wave within the range of, for example, 20 MHz to 180 MHz, 280 MHz to 600 MHz, or 700 MHz to 1000 MHz as a high frequency for the promotion of production with the same structure as that above, and moreover, capable of generating a low frequency electromagnetic wave within the range of, for example, 2±100 kHz as a low frequency for the promotion of production.

Magnetic Treatment Mode Via the Magnetic Treatment Device

Next, the magnetic treatment mode via the above magnetic treatment device 10 of the present embodiment and the effects thereof will be described with reference to FIGS. 5A and 5B. Furthermore, FIGS. 5A and 5B are explanatory diagrams showing the treatment mode employing the above magnetic treatment device 10A, 10B (see FIGS. 2A and 2B) of the present embodiment.

As shown in FIGS. 5A and 5B, the magnetic treatment device 10 is a compact lightweight treatment device (e.g., household treatment device) operated by a battery, such as a dry battery and the like, and as such, easily portable by patients. In addition, this magnetic treatment device 10 is a magnetic stimulation type treatment device that is capable of applying magnetic stimulation to the cells of an affected area within the brain and the like, from outside the body, via the generation of the electromagnetic wave by the abovementioned high frequency coil 30 and the low frequency coil 40. Thus, the magnetic treatment device 10 does not require a particular large unit, or an electrode for passing electric current to human body as with a conventional electrode patch type treatment device, and moreover, the head of the subject does not need to be shaved even when the magnetic stimulation is applied to the inside of the brain, and the like.

When treating the affected area of the human body (the subject to be treated) by employing the above magnetic treatment device 10, for example, as shown in FIGS. 5A(a) and 5B(b), the magnetic treatment device 10 operated by power from the power source may be brought into direct contact with the affected area, or only indirectly brought into contact through hair or clothing, or the like. Thereby, the magnetic treatment device 10 is capable of applying the alternating magnetic field (the high frequency alternating magnetic field and the low frequency alternating magnetic field) generated in the abovementioned manner to the cells of the affected area that are the target of magnetic stimulation. At such a time, the alternating magnetic field provides the magnetic stimulation to these cells, for example, by being applied not only to the cells on the surface of the human body (e.g., hair and skin), but also to the cells inside the human body (e.g., brain, spinal, muscle, blood vessels, and bone).

Moreover, the magnetic treatment device 10, for example, can apply the abovementioned alternating magnetic field to the cells of the affected area even when only brought within the proximity of a position separated from the surface of the body by a predetermined distance, without necessarily requiring that it be brought into direct contact with the affected area, as shown in FIGS. 5A(b) and 5B(b). Specifically, the magnetic treatment device 10 differs, for example, from an electrode patch type magnetic treatment device of direct contact type, and is available as a non-contact type magnetic treatment device that is capable of treatment even from above the hair and clothing, and the like. However, since the intensity of the alternating magnetic field generated by magnetic treatment device 10 decreases along with the increase in the distance from the magnetic treatment device 10 (reduced in proportion to the cube of the distance of separation), the effect of the electromagnetic treatment is weakened when there is an excessive separation between the magnetic treatment device 10 and the affected area.

Thus, in view of the distance of the high frequency coil 30 and low frequency coil 40 from the affected area that is the target of magnetic stimulation (effective distance for providing magnetic stimulation of magnetic field intensity of a minimal level), the magnetic treatment device 10 of the present embodiment is capable of controlling the magnetic field intensity of the high frequency alternating magnetic field and the low frequency alternating magnetic field generated by the high frequency coil 30 and the low frequency coil 40, so as to have an alternating magnetic field with a magnetic field intensity (magnetic flux density) of, for example, 50 nT to 0.01 T applied to the affected area. The magnetic stimulation that can be provided to the cells is sufficiently capable of promoting the production of the neurotrophic factor group, even with the weak magnetic field intensity of 50 nT. Since the magnetic intensity of the earth is approximately 66 mT, the abovementioned magnetic field intensity of 50 nT is an extremely weak intensity, which is approximately $\frac{1}{1000}$ that of the magnetism of the earth.

Hereinafter, a difference between when employing the abovementioned magnetic treatment device 10A (see FIG. 2A) and when employing the magnetic treatment device 10B (see FIG. 2B) will be described. As shown in FIG. 5A, when the abovementioned magnetic treatment device 10A is employed, an alternating magnetic field is generated so that the lines of magnetic force intersect in the longitudinal direction of the magnetic treatment device 10A. Moreover, as shown in FIG. 5B, when the abovementioned magnetic treatment device 10B is employed, an alternating magnetic field is generated so that the lines of magnetic force intersect in the lateral direction of the magnetic treatment device 10B. Accordingly, the magnetic stimulation is capable of deeply and broadly penetrating into the brain of a patient. Moreover, since the magnetic treatment device 10A, 10B generates the alternating magnetic field towards the overall periphery thereof, having the orientation of the magnetic treatment device 10A, 10B oppose the affected area at the time of magnetic treatment allows for a treatment in which the alternating magnetic field is applied to the affected area even in an arbitrary direction, such as a direction that is perpendicular to or oblique to the surface of the body, without being specifically limited to the example in which the direction thereof is parallel to the surface of the body.

By applying the high frequency alternating magnetic field and the low frequency alternating magnetic field to the affected area using the abovementioned magnetic treatment device 10 in the above-indicated manner, for example, the production of the neurotrophic factor group in specific cells of the affected area is promoted, and the recovery of central nervous system cells or cranial nerve cells is stimulated by the neurotrophic factor group, so that an magnetic treatment effect can be produced whereby brain diseases and the like are treated.

At such a time, since the magnetic treatment device 10 intermittently oscillates the abovementioned high frequency electromagnetic wave and the low frequency electromagnetic wave, the alternating magnetic field is intermittently applied to the affected area, so that the effect of the magnetic field can be altered. Thus, the magnetic treatment effect is not weakened due to the tissue of an affected area (cells, and the like) becoming accustomed to a constant magnetic field, such as in a case where the constant alternating magnetic field is continuously generated. Moreover, since the timing for the generation of the high frequency alternating magnetic field and the timing for the generation of the low frequency alternating magnetic field are synchronized, the overall magnetic field applied by the magnetic treatment device 10 has a distinct on/off pattern. Thus, the presence or absence of magnetic stimulation to the affected area is further clarified, so that the magnetic treatment effect can be enhanced.

Furthermore, a rise time and fall time of the magnetic treatment device 10 are extremely small at, for example, no more than 0.003 μsec for the generated high frequency electromagnetic wave, and a rise time and fall time of the low frequency electromagnetic wave that is substantially rectangular are adjusted to no more than 0.1 μsec and no more than 1.0 μsec, for example. Thus, during a change in the abovementioned alternating magnetic field, the rate of change to/from the application/non-application of the magnetic field is rapid. Accordingly, since the tissue of the affected area is sensitized to a change in this magnetic field, the magnetic treatment effect is enhanced.

In addition, the magnetic treatment device 10 provides a feature in which the intensity (magnetic flux density) of the high frequency alternating magnetic field and the low frequency alternating magnetic field applied to the cells of the affected area is, for example, no less than 50 nT to no more than 0.01 T, which is extremely small when compared with that of another conventional magnetic treatment device (e.g., 0.8 T to 10 T). Specifically, when a magnetic field of a high intensity such as that of a conventional magnetic treatment device is employed, damage to the affected area of the brain and the like may occur from the magnetic stimulation. Since damage from such a strong magnetic stimulation is well-known, the safety operation guidelines for a magnetic field environment have been established by industrialized countries. For example, in America (Standford University, 1971), the daily exposure to magnetic stimulation to be applied to a region of the body or the head is made 0.02 T and several minutes per day.

However, a large majority of conventional magnetic treatment methods or magnetic stimulation methods constitute those applying a magnetic field of at least 0.1 T. For example, even the magnetic field intensity of the magnet for the treatment of shoulder stiffness with a diameter of several millimeters is 0.08 T to 0.13 T. As described above, it is undeniable that a conventional magnetic treatment device employing magnetic stimulation via a high intensity magnetic field may cause damage to a living body when used for an extended period of time. Whereas, since the magnetic field intensity applied to the cells of the affected area by the magnetic treatment device 10 of the present embodiment is within the extremely weak range of no less than 50 nT to no more than 0.01 T described above, the possibility of damage being caused to a living body is extremely low. Specifically, a safe magnetic treatment can be provided to an affected area that is important and sensitive, such as the brain.

Nonetheless, it is thought that when the magnetic field intensity of the alternating magnetic field applied to the affected area is excessively low (e.g., less than 30 nT), the magnetic treatment effect thereof is reduced. One theory is that the minimal magnetic field intensity that the cells are capable of reacting to is about 30 nT, for example. In such a case, in order for the magnetic treatment device 10 of the present embodiment to have a magnetic field intensity that is in the preferable range of, for example, 50 nT to 0.01 T applied to the cells of the affected area, the magnetic field intensity of the high frequency alternating magnetic field and the low frequency alternating magnetic field generated by the high frequency coil 30 and the low frequency coil 40 is controlled. The magnetic field intensity of the alternating magnetic fields generated by these coils is determined based on the distance between the affected area which is the target of magnetic stimulation and the high frequency coil 30 as well as the low frequency coil 40 within the magnetic treatment device 10 (e.g., the distance from the surface of the body to the affected area within the brain), the magnetic permeability of the affected area (e.g., the magnetic permeability of the brain), and the like.

Specifically, with regard to the structure of the magnetic treatment device 10B of the present embodiment, when a high frequency alternating magnetic field and a low frequency alternating magnetic field of at least 50 nT are applied to an affected area with a depth of, for example, no more than 6 cm from the surface of the body (specifically, when the effective distance of magnetic stimulation by the magnetic treatment device 10 is 6 cm), the magnetic field intensity of the high frequency alternating magnetic field generated by the high frequency coil 30B in the proximity of the above coil 30B is set at, for example, approximately 0.01 T, and the magnetic field intensity of the low frequency alternating magnetic field generated by the low frequency coil 40B in the proximity of the above coil 40B is set at, for example, no less than approximately 0.1 T. Moreover, when the abovementioned effective distance is 12 cm, the magnetic field intensity of the abovementioned high frequency alternating magnetic field in the proximity of the coil 30B is set at, for example, approximately 0.1 T, and the magnetic field intensity of the abovementioned low frequency alternating magnetic field in the proximity of the coil 40B is set at, for example, approximately 1 T.

As described above, for example, the magnetic treatment device 10 of the present embodiment is capable of applying an alternating magnetic field of a preferred frequency and magnetic field intensity to promote the production of neurotrophic factor group of the cells of the affected area, and of switching between the application/non-application of the above alternating magnetic field at a timing in which the cells are easily susceptible to stimulation. Accordingly, the magnetic treatment device 10 of the present embodiment demonstrates an extremely effective magnetic treatment effect when compared to a conventional magnetic treatment device.

Furthermore, not only is the magnetic treatment device 10 battery-powered, light, compact and easily portable in addition to being easy to operate, it is also capable of easily and quickly (e.g., 10 minutes) achieving the magnetic treatment effect by being brought in direct contact with or into the proximity of the affected area as described above. Accordingly, an magnetic treatment employing the above magnetic treatment device 10 does not require advanced medical technology, such as a cell transplantation to the inside of the brain or injection into the brain, like a conventional regenerative therapy for the brain. Thus, the patient himself/herself is able to use the magnetic treatment device 10 at an arbitrary location, such as home, work, or school, without being admitted to a hospital, so that the treatment can be easily performed at anytime.

In addition, a conventional regenerative therapy, such as a conventional cell transplantation to the inside of the brain or injection into the brain, may lead to brain damage, an infectious disease thereof, or side effects. Whereas, by applying magnetic stimulation to cells functioning to produce neurotrophic factor group from outside the body, the magnetic treatment device 10 of the present embodiment promotes the production of neurotrophic factor group within the above cells and stimulates the independent recovery or proliferation of weakened central nervous system cells or cerebrospinal nervous system cells. Thus, since the insertion of a medical apparatus within the brain is not required, as with a cell transplantation or an injection, it has a significant advantage in which there is no brain damage, infectious diseases thereof, or side effects, and that the effect on the cells or tissue around the affected area is small.

Therapeutic Target of the Magnetic Treatment Device

Next, with respect to the magnetic treatment device 10 of the present embodiment, (1) the cells that are the target of magnetic stimulation, (2) the substances produced via the magnetic stimulation, (3) the site that is the target of treatment, and (4) the disease that is the target of treatment, will be described in detail.

(1) Cells that are Target of Magnetic Stimulation (Cells that are Capable of Producing the Neurotrophic Factor Group)

The cells that are the target of magnetic stimulation via the magnetic treatment device 10 are cells that are capable of producing the neurotrophic factor and/or the neurotrophic factor-like substance. Specifically, the cells that are the target of this magnetic stimulation are, for example, glial cells, neurocytes, fibroblasts, vascular endothelial cells, muscle cells, epidermal cells, keratinocytes, immunocytes, and the like. The primary sites where the cells that are the target of this type of magnetic stimulation exist are, for example, the brain, the spinal cord, nerves, blood vessels, muscles, skin, and the like.

Among these, glial cells (neuroglia) is a generic term of the representative cells producing the neurotrophic factor group, and, for example, there are astrocytes (astroglia), microcytes (microglia), oligodendrocytes, Schwann cells, mantle cells, and the like. Glial cells are present, for example, in the brain, in the periphery of nerve cells, in blood vessels, in muscle, and the like, and the neurotrophic factor group that is produced by the glial cells themselves is supplied to the glial cells or neurocytes, in order to aid in the recovery and proliferation of these cells. Moreover, neurotrophic factor group is also produced by non-nerve related cells present in areas throughout the body, such as the abovementioned fibroblasts, vascular endothelial cells, muscle cells, epidermal cells, immunocytes, and the like.

(2) Substances Produced Via Magnetic Stimulation

When the magnetic stimulation is applied to the above cells that are the target of magnetic stimulation (e.g., glial cells) via the magnetic treatment device 10, the neurotrophic factor and/or neurotrophic factor-like substance is produced in these cells. The physiological effect of this neurotrophic factor and/or neurotrophic factor-like substance is the principal magnetic treatment effect from the magnetic treatment device 10.

The neurotrophic factor (neurotrophin (NT)) is a molecule (protein) supporting the maintenance of the normal function or the survival of the neural cells that are present in the brain, the spinal cord, and peripheral nerves, and which plays an important role in the maintenance, survival, or regeneration of damaged neural cells, or the differentiation or growth of neural cells during a developmental period. This neurotrophic factor may include, for example, a nerve growth factor (NGF), a brain-derived neurotrophic factor (BDNF), a fibroblast growth factor-2 (FGF-2), a glial cell line-derived neurotrophic factor (GDNF), and the like.

The neurotrophic factor-like substance is a substance group other than a neurotrophic factor that promotes neurite outgrowth in neuronal cells. This neurotrophic factor-like substance is a substance supporting the maintenance of the normal function or the survival of the neural cells in a manner similar to that of the abovementioned neurotrophic factor, and has a proteinaceous component and a non-proteinaceous component. For example, the neurotrophic factor-like substance may include, adenosine, adenosine monophosphate (AMP), a manganese ion, genipin (herbal medicine derived low molecular weight substance with plant component), lysophosphatidylethanolamine (animal-plant membrane component), ganglioside, Rho-kinase, and the like. Among these, adenosine and adenosine monophosphate are non-proteinaceous neurotrophic factor-like substances, and Rho-kinase is a proteinaceous neurotrophic factor-like substance.

(3) Site that is Target of Treatment

The therapeutic target site (affected area) of the subject to be treated is the central nervous system (CNS) or the craniospinal nervous system. The central nervous system includes: the telencephalon, the diencephalon, the mesencephalon, the cerebellum, the pons, the medulla oblongata, the spinal cord and blood vessels. The above central nervous system is made up of neurocytes (neurons), glial cells, and blood vessels. Moreover, the craniospinal nervous system is a nerve system composed of cranial nerves and spinal nerves that are part of the peripheral nervous system (PNS). The above craniospinal nervous system is composed of neurocytes (neurons), Schwann cells, and mantle cells. The cells forming the above central nervous system and craniospinal nervous system undergo repair, growth, differentiation, and proliferation via the physiological effect of the neurotrophic factor group supplied from the abovementioned glial cells and the like, to contribute to the treatment of the various diseases indicated below. Moreover, the differentiation of cells is the change in the property and morphology of cells. Furthermore, central nervous system cells are cells that are present in the central nervous system (the telencephalon (cerebral hemisphere), the diencephalon, the mesencephalon, the cerebellum, the pons, the medulla oblongata, the spinal cord and blood vessels). In addition, craniospinal nervous system cells are cells that are present in the craniospinal nervous system.

Moreover, in the subject to be treated (e.g., human body), the site that is the target of the treatment described above and the site that is the target of the magnetic stimulation via the magnetic treatment device 10 may be the same site or may be a different site. For example, the magnetic stimulation may also be applied to the brain (the site that is the target of magnetic stimulation) in order to treat the brain (the site that is the target of treatment). In addition, the magnetic stimulation may also be applied to another site capable of supplying the neurotrophic factor group to the spinal cord in order to treat the spinal cord (the site that is the target of treatment), for example, the femoral region (the site that is the target of magnetic stimulation).

(4) Disease that is Target of Treatment

The disease that is the target of the treatment via the magnetic treatment device 10 is a disease caused by the weakening of, damage to, or a reduction in the number of cells forming the abovementioned central nervous system or craniospinal nervous system (e.g., neurocytes or glial cells), as a result of various factors. Specifically, the disease that is the target of the treatment, for example, is: (a) a neurodegenerative disorder (e.g., Alzheimer's disease, Parkinson's disease, Huntington's disease, amyotrophic lateral sclerosis, multiple sclerosis, multiple system atrophy, and spinocerebellar degeneration); (b) depression; (c) a cerebrovascular disease (e.g., stroke, and cerebral infarction); (d) chronic pain; (e) neuropathic pain; (f) a spinal cord injury (occurring from an external injury or lesion); and the like. Furthermore, although not for a disease, one of the effects of the magnetic treatment via the magnetic treatment device 10 is also, (g) a neuroprotective effect, to prevent these diseases.

Accordingly, the magnetic treatment device 10 of the present embodiment may be available as a neurodegenerative disorder treatment device (e.g., Alzheimer's disease treatment device, Parkinson's disease treatment device, Huntington's disease treatment device, amyotrophic lateral sclerosis treatment device, multiple sclerosis treatment device, multiple system atrophy treatment device, spinocerebellar degeneration treatment device, and the like), a depression treatment device, a cerebrovascular disease treatment device (e.g., stroke treatment device, or cerebral infarction treatment device), a chronic pain treatment device, a neuropathic pain treatment device, a spinal cord injury treatment device, or a device for the prevention of the abovementioned various types of diseases.

For example, when treating depression, an alternating magnetic field is irradiated on the brain of the human body using the abovementioned magnetic treatment device 10, the secretion of BDNF, NGF or the like, from glial cells (e.g., astrocytes) in the brain is promoted, and the neurotrophic factor group is provided to central nervous system cells that have been weakened and the like, so that cellular function is restored by the proliferation or regeneration of peripheral central nervous system cells, and the production of serotonin (endorphin in the brain) is restored, to thereby allow it to contribute to the treatment of depression.

Moreover, when treating Alzheimer's disease, an alternating magnetic field is irradiated on the brain of the human subject using the abovementioned magnetic treatment device 10, the secretion of BDNF, NGF or the like, from glial cells (e.g., astrocytes) of the nucleus basalis of Meynert in the brain where weakening and the like has occurred is promoted, and cerebral cortical cells that have been weakened by β-amyloid deposits are proliferated or regenerated, to thereby allow it to contribute to the treatment of Alzheimer's disease.

Furthermore, when treating a stroke, an alternating magnetic field is irradiated on the brain of the human body using the abovementioned magnetic treatment device 10, the secretion of BDNF, NGF or the like, from glial cells (e.g., astrocytes) of a site that has been damaged by a vascular occlusion and the like is promoted, and the neurotrophic factor group is provided to the damaged cells, so that the neurocytes and glial cells of the damaged area are proliferated and regenerated, to thereby allow it to contribute to the treatment of a stroke.

In addition, when treating neuropathic pain, an alternating magnetic field is irradiated on an affected area in which chronic pain is felt, using the abovementioned magnetic treatment device 10, and the production of BDNF, NGF or the like, is promoted at a peripheral nerve. The above BDNF, NGF or the like, moves inside neurocytes, is transported to dorsal root ganglia or the spinal cord, and the astrocytes are proliferated in the dorsal root ganglia and the spinal cord, to allow the recovery from nervous erethism and allow neuropathic pain to be treated. The above NGF or the like moves inside neurocytes or to a peripheral site at which it is produced, is transported to dorsal root ganglia or to the spinal cord, and repairs or regenerates damaged sensory neurons, to thereby allow it to contribute to the treatment thereof.

Mechanism of the Magnetic Treatment Effect

Figure 6:
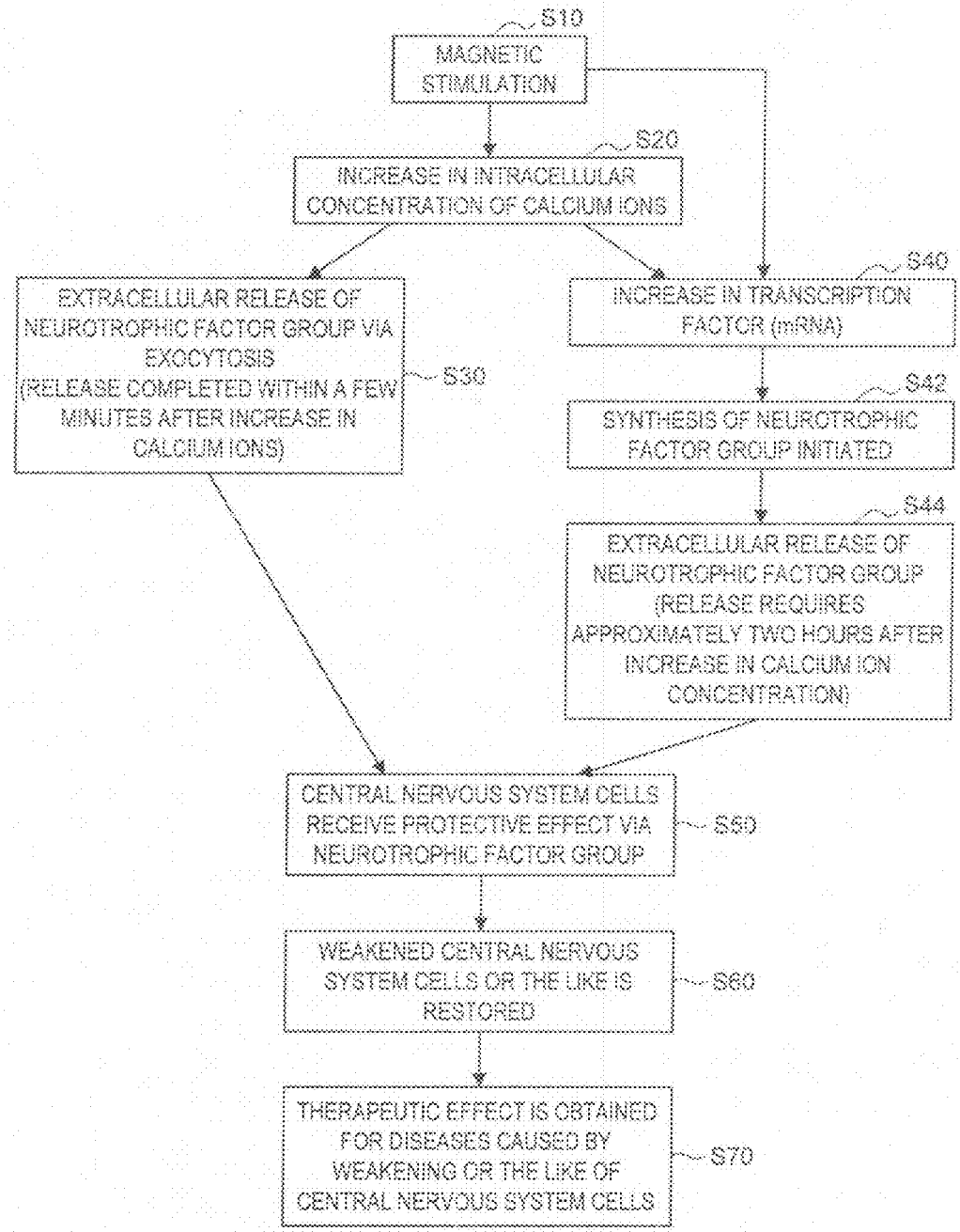
FIG. 6 is a flow chart showing a mechanism of the magnetic treatment effect from the magnetic treatment device of the same embodiment.

Next, the mechanism for achieving the magnetic treatment effect for the abovementioned diseases via magnetic stimulation of the alternating magnetic field from the magnetic treatment device 10 of the present embodiment will be described with reference to FIG. 6. FIG. 6 is a flowchart showing the mechanism of the magnetic treatment effect from the magnetic treatment device 10 of the present embodiment.

In a large sense, the mechanism of the magnetic treatment effect is that a high concentration of the neurotrophic factor and/or the neurotrophic factor-like substance (hereinafter referred to as "neurotrophic factor group") is supplied to central nervous system cells of an area affected with brain disease (e.g. brain), and the regeneration of central nervous system cells is promoted. Specifically, a high frequency alternating magnetic field is irradiated from the magnetic treatment device 10, and magnetic stimulation is applied to cells (the cells that are the target of the abovementioned magnetic stimulation) that are capable of producing the neurotrophic factor group, such as glial cells and the like, so that the production of intracellular neurotrophic factor group is promoted, the neurotrophic factor group produced by these cells are supplied to the cells of an area affected with brain disease, and the like, and the central nervous system cells that have been weakened, damaged, or reduced in number or the like, by a brain disease and the like, are repaired, grown, differentiated, or proliferated.

As shown in FIG. 6, based on the results of cellular experiments, the mechanism of the promotion of production of the neurotrophic factor group is thought to be the simultaneous occurrence of three intracellular processes. These three processes are: (1) the release of the neurotrophic factor group via exocytosis due to an increase in the intracellular concentration of calcium ions (S10→S20→S30); (2) the synthesis and release of neurotrophic factor group via an increase in mRNA due to an increase in the intracellular concentration of calcium ions (S10→S20→S40→S42→S44); and (3) the synthesis and release of neurotrophic factor group via an increase in mRNA that is not due to an increase in the intracellular concentration of calcium ions (S10→S40→S42→S44). Hereinafter, each of these neurotrophic factor group production processes will be described.

(1) Exocytosis

Exocytosis is a cellular function that eukaryotic cells possess, and which functions in the extracellular release of an intracellularly stored substance. Exocytosis also allows the extracellular release of macromolecules, such as proteins.

The process (1) will be described in greater detail. First, with respect to a cell producing neurotrophic factor group, such as glial cells, and the like, magnetic stimulation (S10) from the magnetic treatment device 10 allows a voltage-dependent calcium ion channel or a voltage-independent calcium ion channel that is intracellularly located or located on the surface of a cell membrane to be opened, allows calcium ions from an extracellular or intracellular calcium storage site to be supplied, and allows the intracellular concentration of calcium ions to be increased (S20). The increase in the intracellular concentration of calcium ions allows vacuoles in which intracellular neurotrophic factor group is stored to fuse with a cell membrane, and exocytosis that releases neurotrophic factor group into extracellular spaces to occur (S30). Exocytosis is induced even when the increase in the intracellular concentration of calcium ions is a mere 10%. The release phenomena is started and finished within a few minutes of the increase in the intracellular concentration of calcium ions.

(2) Increase in mRNA Associated with Increase in Intracellular Concentration of Calcium Ions The process (2) is a process arising from the cellular proliferation promoting effect. It is already known in the field of neurology that the neurotrophic factor group is produced even during the cell division stage. The abovementioned magnetic stimulation (S10) allows the intracellular concentration of calcium ions to be increased (S20), to thereby accelerate a cellular growth cycle. The cells in the quiescent stage of the cellular growth cycle pass through the G1 stage to move into the S stage, via the abovementioned increase in the calcium ion concentration. During the S stage, DNA and RNA replication occurs, and mRNA for the production of the neurotrophic factor group is increased (S40: for data demonstrating the evidence, refer to the results of the below-mentioned Experiment 2). The mRNA increased via the above replication allows a neurotrophic factor protein and a partially proteinaceous neurotrophic factor-like substance to be synthesized (S42), and the synthesized neurotrophic factor group to be extracellularly released (S44). The production of the neurotrophic factor group via the process (2) is thought to intensify with time after the magnetic stimulation. It is thought that this is validated by the mechanism of cell division.

(3) Increase in mRNA that is not Due to Increase in Intracellular Concentration of Calcium Ions During the process (3), within the cells receiving the abovementioned magnetic stimulation (S10), mRNA is increased (S40) and neurotrophic factor group is synthesized (S42) and released extracellulary (S44), without being associated with the increase in the intracellular concentration of calcium ions.

Evidence that supports the assumption that the process (3) is occurring will be described. In the below-mentioned Experiment 1, a medium of MB8 cells three hours after the magnetic stimulation (the cells that are the target of magnetic stimulation) was added to PC12 cells (cells that are differentiated by the supply of neurotrophic factor group), and the neurite outgrowth of the PC12 cells was confirmed. The division of MB8 cells employed in Experiment 1 occurs approximately once per day. Since the number of cells moving into the S stage during cultivation three hours after magnetic stimulation under experimental conditions is small, it is thought that the mRNA elevating effect is directly activated by magnetic stimulation, as in the abovementioned process (3). Moreover, in another experiment, experimental data were obtained which showed that the MAP kinase activity within neurocytes increased by approximately 20% after magnetic stimulation was conducted for 10 minutes on cultured neurocytes which were then allowed to stand for an additional 10 minutes. MAP kinase is an enzyme that regulates the activation of proteins within cells, and the synthesis of DNA and RNA in a chain reaction. This chain reaction is referred to as the mitogen-activated protein kinase pathway, and is a reaction system in which a signal is transmitted from the cell membrane to the nucleus. Since the synthesis of a neurotrophic factor protein is promoted when this reaction system is activated, mRNA is also increased.

The abovementioned process (2) is one in which RNA synthesis occurs as a result of an increase in the intracellular concentration of calcium ions. However, in the abovementioned experiment, mRNA is synthesized in a reaction time of 3 hours, and as mandated thereby, the amount of the neurotrophic factor group synthesized is low. Accordingly, in view of such experimental results, it is believed that the process (3) proceeds simultaneously along with the abovementioned process (2).

Next, the mechanism for the production of a non-proteinaceous neurotrophic factor-like substance will be described. Representatives of the neurotrophic factor-like substance include, for example, adenosine, adenosine monophosphate (AMP), a manganese ion, genipin (herbal medicine derived low molecular weight substance with plant component), lysophosphatidylethanolamine (animal-plant membrane component), ganglioside, and Rho-kinase. Although hundreds of types of neurotrophic factor-like substances have been discovered in addition thereto, many of these have not been identified as substances.

These neurotrophic factor-like substances, such as a single ion (e.g., manganese ion), a low molecular weight substance (e.g., adenosine or adenosine monophosphate), a lipid (e.g., lysophosphatidylethanolamine, or a ganglioside), or a proteinaceous component (e.g., Rho-kinase), include a wide variety of properties and types thereof. The synthesis of proteinaceous neurotrophic factor-like substance is promoted under the direction of mRNA, and the proteinaceous neurotrophic factor-like substance is released extracellularly. Whereas, there are many types of non-proteinaceous neurotrophic factor-like substances, and thus the production mechanisms thereof also vary. For example, a neurotrophic factor-like substance of a single ion or low molecular weight substance may be one that exists intracellularly, or may be synthesized intracellularly. In addition, a lipid neurotrophic factor-like substance is synthesized intracellularly. It is thought that both of these non-proteinaceous neurotrophic factor-like substances are released extracellularly via exocytosis. Since the lipid neurotrophic factor-like substance is also a structural component of cell membranes, it is thought that this substance may also be released extracellularly via a process other than exocytosis.

When the neurotrophic factor group is produced in cells (e.g., glial cells) that have received magnetic stimulation via the abovementioned processes (1) to (3), this neurotrophic factor group is supplied to the central nervous system cells and the like that are weakened by a disease and the like, and the central nervous system cells are provided with a protective effect via the neurotrophic factor group (S50). As a result, the central nervous system cells that are weakened and the like are activated and repaired, grown, differentiated, or proliferated (S60), so that a therapeutic effect for a brain disease (e.g., a neurodegenerative disorder, depression, or cerebrovascular disease) caused by the abovementioned weakening of central nervous system cells and the like can be obtained (S70).

According to the above described mechanism, suitable magnetic stimulation is applied to an affected area using the magnetic treatment device 10, so that the production of the neurotrophic factor group within the cells is promoted, to thereby allow a superior treatment or preventive effect to be exerted on various diseases, such as the abovementioned brain diseases and the like.

Based on such a perspective, the magnetic treatment device 10 of the present embodiment is capable of emitting, to be applied to an affected area, an approximately 120 MHz to 160

MHz high frequency alternating magnetic field at a frequency for the production of promotion and approximately 2.0 kHz low frequency alternating magnetic field, with a magnetic flux density of no more than 0.01 T, for example, as an alternating magnetic field capable of providing the desired magnetic stimulation. It is thought that the stimulation by the irradiation of this high frequency alternating magnetic field of approximately 120 MHz to 160 MHz is highly effective in promoting the production of the neurotrophic factor group in cells, when compared to, for example, other frequency bands. Furthermore, it is thought that the stimulation by the irradiation of the 2.0 kHz low frequency alternating magnetic field, for example, functions to release (3-endorphin or cytokine or the like from cells.

Moreover, although the frequency for the production of promotion of the high frequency alternating magnetic field applied to the affected area is preferably approximately 120 MHz to 160 MHz in terms of the magnetic treatment effect according to the below-mentioned experimental results, it was found that the contribution to the increase in the intracellular concentration of calcium ions was sufficient even with frequencies outside of this range. The desired range for the frequency for the promotion of production is 20 MHz to 180 MHz, 280 MHz to 600 MHz, or 700 MHz to 1000 MHz (fourth most preferable range); more preferably 60 MHz to 180 MHz, 280 MHz to 300 MHz, 450 MHz to 550 MHz, or 900 MHz to 950 MHz (third most preferable range); even more preferably 100 MHz to 160 MHz (second most preferable range); and most preferably 120 MHz to 160 MHz (first most preferable range). Among these examples, since a frequency for the production of promotion around the latter range produces even more of the neurotrophic factor group within the cells that are the target of the magnetic stimulation and can supply the neurotrophic factor group to cells of a site that is the target of treatment, the magnetic treatment effect therefrom is significant.

EXAMPLES

Next, the results of experiments that were conducted in order to verify the magnetic treatment effect via the magnetic treatment device 10 of the abovementioned embodiment will be described. As mentioned above, this magnetic treatment device 10 is capable of applying magnetic stimulation on the subject to be treated, by emitting a high frequency alternating magnetic field and a low frequency alternating magnetic field (e.g., 2.0 kHz) at a desired frequency for the promotion of production. Moreover, the below-mentioned examples are to experimentally verify the magnetic treatment effect of the magnetic treatment device 10 of the abovementioned embodiment, and as such, the present invention is not specifically limited to the below-mentioned examples.

Experiment 1

First, Experiment 1, which was conducted in order to determine a suitable range for a high frequency for the promotion of production for the high frequency alternating magnetic field applied to the cells of the subject to be treated via the abovementioned magnetic treatment device 10, will be described.

In the Experiment 1, a high frequency alternating magnetic field of a plurality of different frequencies (20 MHz to 3000 MHz) was applied to the cells that were the target of magnetic stimulation (MB8 cells), the neurotrophic factor group was produced in a culture medium, and then the degree of neurite outgrowth was determined by adding the culture medium containing this neurotrophic factor group to PC12 cells (cells that differentiate with neurites being outgrown (differentiated) via the presence of neurotrophic factor group), to determine the effectiveness of the magnetic treatment of each frequency when compared to an unstimulated group in which no magnetic stimulation was applied.

First, the experimental conditions of the present Experiment 1 and the procedures (1) to (5) thereof will be described.
(1) Cultivation of MB8 Cells and PC12 Cells Glial lineage "MB8 cells" were employed as the cells producing the neurotrophic factor group (the cells that were the target of magnetic stimulation). These MB8 cells are the cells that produce a neurotrophic factor and a neurotrophic factor-like substance. The brain cells of an eight day old mouse were cultured, and glial cells were proliferated, to obtain the MB8 cells. The MB8 cells were plated into a 24-well culture plate (collagen I coated plate) at approximately $15.5 \times 10^5$ cells per well, and cultured for 24 hours in a 5% carbon dioxide environment at 37° C. using a 10% FBS supplemented DMEM culture medium (Manufactured by Nissui Pharmaceutical Co., Ltd.) and a carbon dioxide culture apparatus (incubator).

Moreover, PC12 cells (JCRB0266) were employed as cells for the confirmation of neurite outgrowth. These PC12 cells are adrenal medullary pheochromocytoma cells that are normally employed in nerve growth factor experiments and research. These PC12 cells are the cells in which neurites are outgrown by the presence of nerve growth factor (NGF) and the like, and which initiate the differentiation of neurocytes from adrenal cells via the action of nerve growth factor and the like. Cells that were purchased from the Health Science Research Resources Bank, which is a cell bank, were employed as the PC12 cells. These PC12 cells were plated into a 48-well culture plate (collagen IV coated plate) at approximately $28 \times 10^2$ cells per well (so that the spaces between two cells were not too close), and cultured for 24 hours in a 5% carbon dioxide environment at 37° C. using 10% horse serum and 5% FBS supplemented RPMI-1640 culture medium (Manufactured by Nissui Pharmaceutical Co., Ltd.) and a carbon dioxide incubator. In addition, the below-mentioned cell cultures were all conducted in a 5% carbon dioxide environment at 37° C.
(2) Magnetic Stimulation on MB8 Cells Using an experimental magnetic stimulation device equivalent to the abovementioned magnetic treatment device 10B (refer to FIG. 2B), magnetic stimulation was applied to each of the MB8 cells (cells that produce the neurotrophic factor group) in the above culture plate. The magnetic stimulation was conducted from the lower surface side of the culture plate by using the magnetic stimulation device to irradiate an alternating magnetic field. At such a time, it was incubated for 30 minutes (no magnetic stimulation was applied during the incubation thereof) after having the magnetic stimulation applied for 30 minutes, and then the magnetic stimulation was re-applied for 30 minutes. The frequency of the high frequency alternating magnetic field applied to the MB8 cells in such a manner was incrementally changed at each experimental unit within the range of 20 MHz to 3000 MHz, and each experiment was conducted.

The structure of the experimental magnetic stimulation device employing this magnetic stimulation will be described. This magnetic stimulation device is composed of: a signal generating device ("E4421B", manufactured by Agilent Technologies) for generating a high frequency wave in the MHz frequency band (20 MHz to 3000 MHz); a function generator ("33220A", manufactured by Agilent Technologies) for generating a low frequency wave in the kHz frequency band (2.0 kHz); a function generator ("FG320", manufactured by Yokogawa Electric Co., Ltd.) for generating a low frequency wave in the Hz frequency band (7.81 Hz); an RF-AMP unit (amplifier) regulating output intensity of the signals of these three frequency bands; a control unit integrally controlling the signals of these three frequency bands; and the oscillation coil 50 provided in the abovementioned magnetic treatment device 10B of FIG. 2B.

During magnetic stimulation, as shown in FIG. 7, the abovementioned MB8 cell culture plate 60 was mounted on the oscillation coil 50, and a light shielding cloth was placed thereon. Next, a high frequency electric current and a low frequency electric current were respectively applied to a high frequency coil 30 and a low frequency coil 40 of the oscillation coil 50, and an electromagnetic wave including a high frequency alternating magnetic field and a low frequency alternating magnetic field was generated, to thereby allow magnetic stimulation to be applied for 30 minutes to the MB8 cells within each culture well of the culture plate 60, and then to be stopped for 30 minutes during incubation thereof, and finally re-applied for 30 minutes.

At this time, the frequency of the high frequency electric current applied to the high frequency coil 30 were incrementally changed at each experimental unit within the range of 20 MHz to 3000 MHz, and a high frequency alternating magnetic field at different high frequencies for the production of promotion was applied to the cells. Whereas, the frequency of the low frequency electric current applied to the low frequency coil 40 was maintained at 2.0 kHz, and a low frequency alternating magnetic field at a constant frequency (2.0 kHz) was applied to the cells. Accordingly, the influence of the low frequency alternating magnetic field was eliminated to allow the correlation between the frequency of the high frequency alternating magnetic field and the productivity of the neurotrophic factor group in the MB8 cells to be experimentally tested. Moreover, regardless of the frequency of the high frequency alternating magnetic field, both the high frequency alternating magnetic field and the low frequency alternating magnetic field were intermittently output at 7.81 Hz, as shown in the abovementioned FIG. 4. Furthermore, when the magnetic field intensity (magnetic flux density) of the center portion of the abovementioned oscillation coil 50 during magnetic stimulation was measured, the magnetic field intensity of the 83.3 MHz high frequency electromagnetic wave was 1.26 µT, and the magnetic field intensity of the low frequency electromagnetic wave was 13 µT.

(3) the Cultivation of MB8 Cells after Magnetic Stimulation, and the Production of the Neurotrophic Factor Group Each of the MB8 cells (the cells producing the neurotrophic factor group) of the magnetically stimulated group that received the magnetic stimulation at each frequency of the abovementioned (2) was incubated for 3 hours at 37° C. using the abovementioned culture plate. During the cultivation, the MB8 cells produced a neurotrophic factor group in the amount according to each frequency at the time the abovementioned magnetic stimulation is received, and released it extracellularly. Furthermore, the MB8 cells of the unstimulated group in which the magnetic stimulation of the abovementioned (2) was not implemented were also cultured under similar conditions to those of the magnetically stimulated group.

(4) Provision of Neurotrophic Factor Group to PC12 Cells, and Neurite Outgrowth

After the cultivation of the abovementioned (3), the culture medium of each of the MB8 cells (including the neurotrophic factor group produced by the MB8 cells) of the magnetically stimulated group was aspirated, filtered with a microfilter, and then each post-filtered culture medium was added to the PC12 cells. Afterwards, each of the PC12 cells was cultured at 37° C. for 24 hours. During the cultivation, the neurites of each of the PC12 cells were formed and outgrown, depending on the amount of the neurotrophic factor group present within the culture medium. Furthermore, the PC12 cells to which the culture medium of the MB8 cells of the unstimulated group was added were also cultured in a similar manner.

(5) Determination of Neurite Outgrowth in PC12 Cells

Each of the cultured PC12 cells after the cultivation of the abovementioned (4) was observed with a microscope, and cells in which the length of the neurites was outgrown by at least one cell length were determined as positive cells. Three hundred PC12 cells were observed for each cell group that was magnetically stimulated at each frequency, and the number of positive cells was recorded. In addition, the PC12 cells of the unstimulated group were also similarly determined, and the number of positive cells was recorded.

Then, based on the below-mentioned formula, the effectiveness of the magnetic stimulation at each of the abovementioned frequencies was determined. This effectiveness provides an indication of the degree of neurite outgrowth of the PC12 cells of the magnetically stimulated group as compared to that of the PC12 cells of the unstimulated group, i.e., an indication of the degree of neurite outgrowth of the PC12 cells via magnetic stimulation (magnetic treatment effect) at each frequency. Specifically, the higher the effectiveness, the greater the amount of the neurotrophic factor group produced (high degree of neurotrophic factor group productivity) within the MB8 cells via magnetic stimulation, which indicates that the neurites of the PC12 cells are outgrown (high degree of neurite outgrowth) via the neurotrophic factor group. This indicates that, by supplying a high concentration of the neurotrophic factor group, the repair, growth, differentiation, or proliferation of central nervous system cells or craniospinal nervous system cells weakened and the like as a result of a disease was promoted, to thereby provide a highly effective magnetic treatment for a disease.

(Effectiveness)=(Number of positive cells of the magnetically stimulated group)/(Number of positive cells of the unstimulated group)

In addition, after the neurite outgrowth effect described above was obtained for each experimental unit, these effects were totaled for each same frequency, and the average effectiveness at neurite outgrowth (number of times that of the unstimulated group) was determined.

Moreover, the present Experiment 1 was conducted a total of 2,173 times at all frequencies. When the experimental data from each of these experiments were totaled, the data indicating that the neurite outgrowth might be related to a factor other than magnetic stimulation (e.g., poor cell culture, specific experimental data that deviated considerably from other experimental data for the same frequency) were eliminated from the total. On each day of the present Experiment 1, experiments relating to the confirmation of the neurite outgrowth of the unstimulated group, the confirmation of the neurite outgrowth at the time of magnetic stimulation at 135 MHz, and the confirmation of the neurite outgrowth at the time of magnetic stimulation by any one of the frequencies employed in the experiment of the previous day were conducted again, to ensure the accuracy thereof.

Furthermore, the PC12 cells employed in the abovementioned Experiment 1 demonstrate a property whereby differentiation from adrenal cells into neurocytes is initiated by the action of the nerve growth factor and the like, and the differentiation of these PC12 cells into neurocytes can be easily determined based on the neurite outgrowth. The reaction producing the neurotrophic factor group has several mechanisms, and each reaction thereof is carried out via the interaction of several reactions (cascade reaction). In the present Experiment 1, rather than investigating each of these mechanisms and reactions, the degree of occurrence of neurite outgrowth phenomena that are critical to a living subject and for overall consequent nerve function was studied. Specifically, even if the abovementioned individual reactions relating to the production of neurotrophic factor group are promoted, since it is thought that the value as a treatment would be low if there was no neurite outgrowth as a consequence, the degree of neurite outgrowth at each frequency was measured as an indicator showing the magnetic treatment effect therefrom.

As described above, the experimental conditions and experimental procedures of Experiment 1 were described. The experimental results of the Experiment 1 are shown in Table 1 and FIG. 8. Furthermore, the graph of FIG. 8 illustrates an approximate curve, by plotting the experimental data of the average effectiveness (number of times that of the unstimulated group) shown in Table 1 at each frequency (MHz).

Moreover, the meaning of each parameter of the above Table 1 and FIG. 8 is as follows:

"Frequency (MHz)" is a frequency of a high frequency electromagnetic wave generated by the abovementioned magnetic stimulation device, i.e., a frequency of the high frequency alternating magnetic field applied to the MB8 cells; and "Effectiveness" is the value of the effectiveness of the magnetically stimulated group divided by the effectiveness of the unstimulated group and averaged for each frequency, and indicates how many number of times the neurite outgrowth effect of the magnetically stimulated group via the high frequency alternating magnetic field of each frequency is, compared to that of the unstimulated group.

As shown in Table 1 and FIG. 8, when the frequency of the high frequency alternating magnetic field applied to the MB8 cells (the cells that are target of the magnetic stimulation) is within the range of 120 MHz to 160 MHz (the first most preferable range), the effectiveness on the neurite outgrowth of the PC12 cells via the neurotrophic factor group is at least

TABLE 1

| FREQUENCY (MHz) | EFFECTIVENESS (Number of Times) | | | | |
|---|---|---|---|---|---|
| UNSTIMULATED GROUP | 1 | | | | |
| 20 | 2.1 | | | | ↑20 MHz |
| 40 | 1.93 | | | | |
| 60 | 2.58 | | | ↑60 MHz | |
| 80 | 2.8 | | | | FOURTH MOST PREFERABLE RANGE (AT LEAST 2 TIMES THE EFFECTIVENESS) |
| 100 | 3.32 | | ↑100 MHz | THIRD MOST PREFERABLE RANGE (AT LEAST 2.5 TIMES THE EFFECTIVENESS) | |
| 120 | 3.54 | ↑120 MHz FIRST MOST PREFERABLE RANGE (AT LEAST 3.5 TIMES THE EFFECTIVENESS) | SECOND MOST PREFERABLE RANGE (AT LEAST 3 TIMES THE EFFECTIVENESS) | | |
| 135 | 3.47 | | | | |
| 160 | 3.57 | ↓160 MHz | ↓160 MHz | | |
| 180 | 2.85 | | | ↓180 MHz | ↓180 MHz |
| 200 | 1.67 | | | | |
| 220 | 1.73 | | | | |
| 240 | 1.56 | | | | |
| 260 | 1.7 | | | | |
| 280 | 2.7 | | | 280 MHz ↑ THIRD MOST PREFERABLE RANGE (AT LEAST 2.5 TIMES THE EFFECTIVENESS) | ↑280 MHz FOURTH MOST PREFERABLE RANGE (AT LEAST 2 TIMES THE EFFECTIVENESS) |
| 300 | 2.85 | | | 300 MHz ↓ | |
| 350 | 2.48 | | | | |
| 400 | 2.18 | | | | |
| 450 | 2.6 | | | 450 MHz ↑ THIRD MOST PREFERABLE RANGE (AT LEAST 2.5 TIMES THE EFFECTIVENESS) | |
| 500 | 2.75 | | | | |
| 550 | 2.82 | | | 550 MHz ↓ | |
| 600 | 2.38 | | | | ↓600 MHz |
| 650 | 1.87 | | | | |
| 700 | 2.29 | | | | ↑700 MHz FOURTH MOST PREFERABLE RANGE (AT LEAST 2 TIMES THE EFFECTIVENESS) |
| 750 | 2.24 | | | | |
| 800 | 2.19 | | | | |
| 850 | 2.28 | | | | |
| 900 | 2.81 | | | 900 MHz ↑ THIRD MOST PREFERABLE RANGE (AT LEAST 2.5 TIMES THE EFFECTIVENESS | |
| 950 | 2.56 | | | 950 MHz ↓ | |
| 1000 | 2.45 | | | | ↓1000 MHz |
| 1500 | 1.62 | | | | |
| 2000 | 2.1 | | | | |
| 2500 | 2.5 | | | | |
| 3000 | 2.6 | | | | |

3.5 times that of the unstimulated group, which is extremely high, especially, when the abovementioned frequency is 140 MHz to 160 MHz, the effectiveness is at the highest peak of approximately 3.6 times that of the unstimulated group. Accordingly, when magnetic stimulation of the high frequency alternating magnetic field within the abovementioned first most preferable range is applied, the outgrowth of PC12 cell neurites that can be promoted is at least 3.5 times that of a case in which no magnetic stimulation is applied, and as such, an extremely remarkable magnetic treatment effect is exerted.

Furthermore, when the frequency of the high frequency alternating magnetic field applied to the MB8 cells (the cells that are the target of the magnetic stimulation) is within the range of 100 MHz to 160 MHz (the second most preferable range), the effectiveness of the neurite outgrowth of the PC12 cells via the neurotrophic factor group is at least 3.0 times that of the unstimulated group, which is extremely high. Accordingly, when magnetic stimulation of the high frequency alternating magnetic field within the abovementioned second most preferable range is applied, the outgrowth of the PC12 cell neurites that can be promoted is at least 3.0 times that of a case in which no magnetic stimulation is applied, and as such, an extremely remarkable magnetic treatment effect is exerted.

In addition, when the frequency of the high frequency alternating magnetic field is within the range of 60 MHz to 180 MHz, 280 MHz to 300 MHz, 450 MHz to 550 MHz, or 900 MHz to 950 MHz (the third most preferable range), the effectiveness of the neurite outgrowth of PC12 cells via the neurotrophic factor group is at least 2.5 times that of the unstimulated group, which is very high. Accordingly, when magnetic stimulation of the high frequency alternating magnetic field within the abovementioned third most preferable range is applied, the outgrowth of the PC12 cell neurites that can be promoted is at least 2.5 times that of a case in which no magnetic stimulation is applied, and as such, an extremely remarkable magnetic treatment effect is exerted.

Moreover, when the frequency of the high frequency alternating magnetic field is within the range of 20 MHz to 180 MHz, 280 MHz to 600 MHz, or 700 MHz to 1000 MHz (the fourth most preferable range), the effectiveness of the neurite outgrowth of PC12 cells via the neurotrophic factor group is at least 2.0 times that of the unstimulated group. Accordingly, when magnetic stimulation of a high frequency alternating magnetic field within the abovementioned fourth most preferable range is applied, the outgrowth of PC12 cell neurites that can be promoted is at least 2.0 times that of a case in which no magnetic stimulation is applied, and as such, an extremely remarkable magnetic treatment effect is exerted.

Furthermore, the neurotrophic factor group that is produced in vivo is released from the cells producing neurotrophic factor group, and passes through intercellular spaces to reach the site requiring the neurotrophic factor group (the site that is the target of treatment). During this passage thereof, although a molecule of the neurotrophic factor group passes therebetween, liquid components are reduced (this phenomenon is referred to as "bioconcentration"). Accordingly, when the neurotrophic factor group reaches the site where it is required, since it is more concentrated than the concentration at the time of the production, the magnetic treatment effect is further intensified.

According to the results of Experiment 1 described above, from the perspective of the magnetic treatment effect, it is desirable that the high frequency for the promotion of production of the high frequency alternating magnetic field applied to the cells producing the neurotrophic factor group of the MB8 cells and the like (the cells that are the target of magnetic stimulation) is preferably within the abovementioned fourth most preferable range, more preferably within the third most preferable range, even more preferably within the second most preferable range, and most preferably within the first most preferable range. Specifically, by applying a high frequency alternating magnetic field with a frequency in such a range, the production of the neurotrophic factor group via the abovementioned cells producing neurotrophic factor group is significantly promoted, so that a high concentration of neurotrophic factor group is supplied to the central nervous system cells or craniospinal nervous system cells existing in the periphery thereof and the like, and the outgrowth of the neurites of these cells can be increased by at least 2.0, 2.5, 3.0, or 3.5 times that of the unstimulated group. Accordingly, the central nervous system cells or craniospinal nervous system cells that are weakened, damaged, or reduced as a result of a brain disease and the like can be repaired, grown, differentiated, or proliferated, and the brain disease and the like can be suitably treated or prevented, to thereby provide a highly efficient magnetic treatment.

Experiment 2

Next, Experiment 2, which was conducted in order to verify that intracellular mRNA is increased and that the synthesis of the neurotrophic factor group is promoted via the magnetic stimulation by the abovementioned magnetic treatment device 10, will be described. In Experiment 2, an increase in the expression of intracellular mRNA after magnetic stimulation at 135 MHz was verified via a reverse transcriptase-polymerase chain reaction method (RT-PCR method).

First, the experimental conditions of Experiment 2 and the procedures (1) to (7) thereof will be described.

(1) Cultivation of MB8 Cells

"MB8 cells", which are glial lineage cells, were employed as the cells producing the neurotrophic factor group (the cells that were the target of magnetic stimulation). The cultivation of these MB8 cells was conducted in a similar manner to the cell cultivation of the abovementioned Experiment 1.

(2) Magnetic Stimulation of MB8 Cells

Using a magnetic stimulation device similar to that of the abovementioned Experiment 1 (refer to FIG. 7), a high frequency alternating magnetic field (135 MHz) and a low frequency alternating magnetic field (2.0 kHz) were irradiated on the MB8 cells, and magnetic stimulation was applied thereto for 20 minutes.

(3) Cultivation of MB8 Cells after Magnetic Stimulation

The MB8 cells that received the magnetic stimulation of the abovementioned (2) were incubated for 3 hours at 37° C., and mRNA production was promoted inside the MB8 cells.

(4) Extraction of RNA

After the abovementioned cultivation, the culture medium was discarded and an RNA extraction liquid (ISOGEN) was added. Next, the MB8 cells were crushed by a homogenizer, and allowed to stand for 5 minutes at room temperature. Afterwards, chloroform was added to this suspension, it was allowed to stand for 10 minutes at room temperature, and then centrifuged at 12000×g for 15 minutes at 4° C. After that, the supernatant was collected, the same amount of inopropanol as the supernatant was added thereto, it was allowed to stand for 10 minutes at room temperature, and then centrifuged again at 12000×g for 15 minutes at 4° C. Then, it was rinsed by adding 1 ml of 70% ethanol to the precipitate obtained therefrom, and centrifuged at 12000×g for 5 minutes at 4° C. Thereafter, the precipitate was vacuum dried for 15 minutes in a desiccator, then sufficiently dissolved by adding a DEPC treated Tris-HCl/EDTA solution, to obtain an RNA solution.

(5) Amplification of RNA via RT-PCR Method

The abovementioned RNA solution, a 10 μM primer, and ultra-pure water were placed in a PCR tube, and reacted for 2 minutes at 72° C. Next, 10 mM of deoxynucleotide triphosphate solution (dNTP), 100 mM of dithiothreitol solution (DTT), and 200 unit/μl of reverse transcriptase solution were added, and a reverse transcription reaction was conducted for 60 minutes at 42° C. Afterwards, a Tris-HCl/EDTA solution was added, heat treatment was conducted for 7 minutes at 72° C., and a single strand cDNA solution was obtained. Ultra-pure water, PCR buffer, 25 mM $MgCl_2$, 2.5 mM dNTP mixture, 10 μM each of two primer types, and Taq polymerase, were added to this single strand cDNA solution, which was placed in a PCR tube and reacted for 3 minutes at 94° C. Then, denaturation was performed for 30 seconds at 94° C., annealing was performed for 1 minute at 45° C., and chain elongation was performed for 45 seconds at 72° C., and the abovementioned reactions, as a single cycle, were repeated for 40 minutes. After that, reaction at 72° C. for 5 minutes was conducted, and chain elongation reaction was concluded.

(6) Separation and Detection of RNA (Electrophoresis)

After the abovementioned chain elongation reaction was completed, a loading buffer was added, and RNA was separated by size via electrophoresis on 2% (w/v) agarose gel containing ethidium bromide.

(7) Quantitative Determination of RNA

After the abovementioned electrophoresis, the separated RNA was fluoresced, translated into an image by a "Molecular Imaging FX (manufactured by Bio-Rad Laboratories, Inc.)", and mRNA was quantified using "Image J" software.

In addition, the increased expression of the intracellular mRNA of the MB8 cells of the unstimulated group in which magnetic stimulation was not applied was also quantified in a similar manner to that of the cells of the abovementioned magnetically stimulated group. Thus, the degree of increase in mRNA (the number of times that of the unstimulated group) was determined by dividing the amount of mRNA of the magnetically stimulated group by the amount of mRNA of the magnetically stimulated group. The degree of increase in mRNA was determined two times each for BDNF mRNA and for NGF mRNA.

As described above, the experimental conditions and experimental procedures of Experiment 2 were described. Then, the experimental results of the abovementioned Experiment 2 will be described. These experimental results are shown in FIG. 9.

As shown in FIG. 9, with regard to BDNF mRNA, the cells of the magnetically stimulated group showed expression that was 2.78 times that of the unstimulated group in the first experiment, and 2.06 times (an average of 2.42 times) that of the unstimulated group in the second experiment (i.e., increase in BDNF mRNA). Furthermore, with regard to NGF mRNA, the cells of the magnetically stimulated group showed expression that was 2.20 times that of the unstimulated group in the first experiment, and 1.52 times (an average of 1.86 times) that of the unstimulated group in the second experiment (i.e., increase in NGF mRNA).

According to these experimental results, it was verified that, via magnetic stimulation, using the abovementioned magnetic treatment device 10, with a high frequency alternating magnetic field of 135 MHz, mRNA for producing BNDF or NGF within the cells producing the neurotrophic factor group was significantly increased when compared to the unstimulated group. Thus, by applying magnetic stimulation via the abovementioned magnetic treatment device 10, a large amount of BDNF, or NGF neurotrophic factor or the like is synthesized via the increase in mRNA within the cells producing the neurotrophic factor group, and it is released extracellularly.

Experiment 3

Hereinafter, Experiment 3, which was conducted in order to verify the intracellular occurrence of exocytosis via magnetic stimulation by the abovementioned magnetic treatment device 10, will be described.

Exocytosis occurs after an increase in the intracellular concentration of calcium ions, and begins and ends within a few minutes. Whereas, the time required for mRNA to be increased via magnetic stimulation, to transmit the neurotrophic factor group production instructions to the organ in charge of production, and to produce the neurotrophic factor group (synthesis and extracellular release thereof) is approximately two hours. By utilizing the time difference between both of these, the presence or absence of a process involving exocytosis (S20→S30 of the above FIG. 6) and a process involving mRNA (S40 to S44), with regard to the intracellular production of neurotrophic factor group could be confirmed.

Therefore, similarly to the abovementioned Experiment 1, the present Experiment 3 determined: (1) cell culture; (2) magnetic stimulation; (4) cultivation of PC12 cells; and (5) neurite outgrowth. However, in (3) the cultivation of MB8 cells after magnetic stimulation of Experiment 3, the times that the MB8 cells were left to stand after magnetic stimulation (time of producing neurotrophic factor group) were set at 10 minutes (10 minute standing group) and 3 hours (3 hour standing group). Although exocytosis occurred in the MB8 cells in the short time span of 10 minutes, the synthesis of the neurotrophic factor group accompanying an increase in mRNA did not occur. Thus, the results of the above Experiment 3 prove that when the neurites of the PC12 cells of the 10 minute standing group were outgrown, exocytosis occurred in the MB8 cells, and the neurotrophic factor group was released.

First, the experimental conditions of Experiment 3 and the procedures (1) to (5) thereof will be described.

(1) Cell Culture

Similarly to (1) of the abovementioned Experiment 1, the MB8 cells that were the target cells of magnetic stimulation (cells producing the neurotrophic factor) and the PC12 cells that were the cells used for confirmation of neurite outgrowth were both cultured for 24 hours.

(2) Magnetic Stimulation

Using a magnetic stimulation device similar to that of the abovementioned Experiment 1 (refer to FIG. 7), magnetic stimulation was applied to the MB8 cells within the abovementioned culture plate for 30 minutes, followed by 30 minutes of cultivation (no magnetic stimulation was applied during the cultivation), and then the re-application of the magnetic stimulation for 30 minutes. At such a time, the frequency of the high frequency alternating magnetic field that was applied to the MB8 cells was 120 MHz.

(3) Allowing the Cells to Stand after Magnetic Stimulation

The culture plate of the abovementioned post-magnetic stimulation MB8 cells of the 10 minute standing group was allowed to stand for 10 minutes in a carbon dioxide culture apparatus with a 5% carbon dioxide concentration at 37° C., while the 3 hour standing group was allowed to stand for 3 hours. Accordingly, in the 10 minute standing group, the neurotrophic factor group was released into the culture medium via exocytosis. Whereas, in the 3 hour standing group, the release of the neurotrophic factor group via exocytosis and the production and release of the neurotrophic factor group via other processes (synthesis and release via an increase in mRNA) are both occurred. After the production of this neurotrophic factor group, the entire culture medium of the MB8 cells of the abovementioned 10 minute standing group and 3 hour standing group was aspirated, the culture media thereof were filtered with a microfilter, and a culture medium to be added to the PC12 cells was obtained.

(4) Cultivation of PC12 Cells

The culture media of the PC12 cells cultured via the abovementioned (1) were removed by aspiration, and the culture medium of the 10 minute standing group and the culture medium of the 3 hour standing group obtained via (3) were individually added. After that, the PC12 cells with each culture medium added thereto were individually cultured for 24 hours in a carbon dioxide culture apparatus with a 5% carbon dioxide concentration at 37° C.

(5) Determination of Neurite Outgrowth in PC12 Cells

Twenty-four hours after the time at which each of the culture media obtained by (3) was individually added to the PC12 cells in the abovementioned (4), similarly to the abovementioned Experiment 1, the number of positive PC12 cells in which neurites were outgrown was counted, and the neurite outgrowth ratio (ratio of positive cells) was calculated.

As described above, the experimental conditions of Experiment 3 and the procedures thereof were described. Then, the experimental results of the above Experiment 3 will be described with reference to Table 2.

TABLE 2

| Sample | Neurite Outgrowth Ratio (%) |
|---|---|
| Unstimulated Group | 7.4% |
| Post-Magnetic Stimulation 10 Minute Standing Group | 15.5% |
| Post-Magnetic Stimulation 3 Hour Standing Group | 27.9% |

As shown in Table 2, the neurite outgrowth ratio of the PC12 cells was 7.4% in the unstimulated group (reference group) in which no magnetic stimulation is applied. Whereas, the post-magnetic stimulation 10 minute standing group had an outgrowth ratio of 15.5%, which was 2.1 times that of the unstimulated group. Accordingly, exocytosis occurred in the post-magnetic stimulation MB8 cells within a short time period of 10 minutes, so that the production of the neurotrophic factor group could be verified.

Moreover, the post-magnetic stimulation 3 hour standing group had an outgrowth ratio of 27.9%, which was 3.8 times that of the unstimulated group and 1.8 times that of the 10 minute standing group. Accordingly, the fact that the production of the neurotrophic factor group occurred in the post-magnetic stimulation MB8 cells via a process other than exocytosis could be verified.

Experiment 4

Next, Experiment 4, which was conducted in order to verify that the intracellular concentration of calcium ions was increased via magnetic stimulation by the abovementioned magnetic treatment device 10, will be described. In the Experiment 4, cells were collected from each region of a bovine brain, magnetic stimulation was applied to each of these cells at 83.3 MHz, 2 kHz, and 7.8 Hz, and the regions of cells in the brain in which an increase in the intracellular concentration of calcium ions was confirmed and the positive reaction thereof were verified.

First, the experimental conditions of the present Experiment 4 and the procedures (1) to (5) thereof will be described.

(1) Collection and Cultivation of Cells

Brain slices were anatomically collected from each region of the bovine brain (frontal lobe region of the cerebral cortex, temporal lobe region of the cerebral cortex, cerebellum and medulla oblongata regions, and hippocampus), and the cells thereof were primarily cultured as test cells in accordance with a typical brain cell culture method.

(2) Loading of Calcium Fluorescent Indicator

A Fluo-3 calcium fluorescent indicator (Manufactured by Dojindo Molecular Technologies, Inc.) was employed to measure the intracellular concentration of calcium ions. The calcium fluorescent probe (Fluo-3) was added to the abovementioned test cells cultured in a glass-base dish to bring the final concentration thereof to 4 µM, then loaded for 30 minutes at 37° C., washed 3 times with the standard solution, and measurements were obtained. The composition of this reference solution was 135 mM NaCl, 2.8 mM KCl, 1.8 mM $MgCl_2$, 10 mM D-glucose, 10 mM HEPES (pH=7.3).

(3) Magnetic Stimulation

A glass-base dish into which cells were placed after the loading of the abovementioned (2) was mounted on an inverted microscope. The oscillation coil 50 shown in the abovementioned FIG. 7 was mounted on the lid of this glass-base dish, and magnetic stimulation was applied to the cells for 10 minutes. During this magnetic stimulation, the 83.3 MHz high frequency alternating magnetic field and the 2 kHz low frequency alternating magnetic field were intermittently irradiated at 7.8 Hz onto the cells, as shown in FIG. 4.

(4) Measurement of the Distribution of Intracellular Fluorescence

Using an inverted microscope, the magnetically stimulated cells that were loaded and stained with the abovementioned fluorescent dye were observed at room temperature (25° C.). A 20- to 40-fold objective lens was used to allow the fluorescent intensity of at least ten cells to be measured simultaneously. The fluorescence from the irradiation of excited light was detected with a digital CCD camera (Product name: Hi SCA, manufactured by Hamamatsu Photonics K.K.). The fluorescent intensity ratio of the cells was analyzed with a time plus system (Product name: AQUACOSMOS, manufactured by Hamamatsu Photonics K.K.).

Before applying the magnetic stimulation of the abovementioned (3), a change in the fluorescent intensity of the cells that was within 1±0.05 was confirmed for at least 5 minutes. Next, a change in the intracellular concentration of calcium ions was observed for a period of 30 minutes, after the magnetic stimulation of the abovementioned (3) was applied for 10 minutes. Then, 600 mM potassium chloride of only the amount of one-tenth of the volume of liquid in the glass-base dish. Before, during, and after the magnetic stimulation, and after the addition of potassium chloride, the series of reactions was continued, and intracellular fluorescence intensity distribution was measured and observed.

(5) Determination of Experimental Success or Failure

Regarding the addition of the abovementioned potassium chloride, only in a case where the cells showed a dramatic increase in the concentration of calcium ions, the experimental data of such cells were employed. Regarding the addition of potassium chloride, since the cells not showing a normal reaction in which there was a dramatic increase in the concentration of calcium ions failed to demonstrate a normal calcium response, the experimental data thereof were not employed.

(6) Determination

After the magnetic stimulation, in cases where there was at least one cell in which the intracellular fluorescence intensity increased at least 10% more than before the magnetic stimulation, it was judged as a positive reaction (i.e., the intracellular concentration of calcium ions was increased via the magnetic stimulation).

As described above, the experimental conditions and the experimental procedures of Experiment 4 were described. Next, the experimental results of Experiment 4 will be described with reference to Table 3.

TABLE 3

| Regions of Cells Inside Brain | Positive Reaction Rate (n: Number of Samples) |
| --- | --- |
| Frontal Lobe Region of Cerebral Cortex | 57.5% (n = 33) |
| Temporal Lobe Region of Cerebral Cortex | 45.4% (n = 22) |
| Cerebellum and Medulla Oblongata Regions | 15.3% (n = 13) |
| Hippocampus | 5.2% (n = 19) |

As shown in Table 3, the increase in the intracellular concentration of calcium ions (positive reaction rate) via magnetic stimulation was relatively high in the frontal lobe region of the cerebral cortex at 57.5%, and the temporal lobe region of the cerebral cortex at 45.4. Accordingly the cells of these regions in the brain were verified as having an increased intracellular concentration of calcium ions via magnetic stimulation. At such a time, the increase in the intracellular concentration of calcium ions via magnetic stimulation means that the exocytosis of the abovementioned cells can be induced and the release of the neurotrophic factor group can be promoted.

On the other hand, the increase in the intracellular concentration of calcium ions (positive reaction rate) was relatively low in the cerebellum and medulla oblongata regions at 15.3%, and in the hippocampus at 5.2%. Accordingly, it was clear that the increase in the intracellular concentration of calcium ions via magnetic stimulation differed depending on the regions within the brain from which cells were collected.

Experiment 5

Next, Experiment 5, which was conducted in order to verify the production of substance (i.e., a neurotrophic factor-like substance) that demonstrates a neurite outgrowth effect other than the neurotrophic factor via magnetic stimulation by the abovementioned magnetic treatment device 10, will be described.

In addition to the abovementioned various types of neurotrophic factors, adenosine, adenosine monophosphate (AMP), a manganese ion, genipin, lysophosphatidylethanolamine, Rho-kinase and the like are known as substances that demonstrate an effect whereby the neurites of the neural cells are outgrown. The present experiment 5 was conducted to confirm whether a substance (a neurotrophic factor-like substance) that demonstrates a neurite outgrowth effect other than the neurotrophic factor, and the neurotrophic factor are produced via magnetic stimulation on MB8 cells.

Since neurotrophic factor is protein, it is easily denatured via the application of heat, and the neurite outgrowth effect is lost. A proteinaceous component and a non-proteinaceous component are present in the neurotrophic factor-like substance. The non-proteinaceous component does not lose its neurite outgrowth effect via the application of heat. Thus, in the present Experiment 5, a post-magnetically stimulated culture medium of the MB8 cells to which heat was applied and one to which heat was not applied were added to the PC12 cells, individually, and the degree of neurite outgrowth of the PC12 cells to which the heated culture medium (heated group) was added and the degree of neurite outgrowth of the PC12 cells to which the unheated culture medium (unheated group) was added were compared to confirm the presence of the neurotrophic factor or the neurotrophic factor-like substance. If the neurites of the PC12 cells to which the heated culture medium was added are outgrown, the existence of the neurotrophic factor-like substance can be verified thereby.

(1) Cultivation of MB8 Cells

The culture medium of MB8 cells cultured in a similar manner to that of the abovementioned Experiment 1 was sampled, and 400 µl of serum-free RPMI was added thereto.

(2) Magnetic Stimulation on MB8 Cells

Using a magnetic stimulation device similar to that of the abovementioned Experiment 1 (refer to FIG. 7), magnetic stimulation by a high frequency alternating magnetic field (135 MHz) was applied to the abovementioned MB8 cells for 30 minutes, which were then incubated for 30 minutes under a 5% carbon dioxide concentration at 37° C. (no magnetic stimulation was applied during the cultivation), and afterwards again subjected to 30 minutes of magnetic stimulation.

(3) Cultivation of MB8 Cells after Magnetic Stimulation, and Production of Neurotrophic Factor Group Each of the MB8 cells (cells producing the neurotrophic factor group) of the magnetically stimulated group receiving the magnetic stimulation at each frequency of the abovementioned (2) was cultured for 3 hours under a 5% carbon dioxide concentration at 37° C.

(4) Heating of Culture Medium

After the cultivation of the abovementioned (3), the entire volume of the culture medium of the MB8 cells (including the neurotrophic factor group produced by the MB8 cells) was collected in a microtube, and heated for 2 minutes in 90° C. oil bath. After 2 minutes of this heating, the microtube was taken out and rapidly cooled in an ice water for 1 minute. The neurite outgrowth effect of the neurotrophic factor (protein) included in the culture medium was lost via this heating process.

(5) Filtration of Culture Medium

Fetal bovine serum (FBS) was added to the culture medium obtained via the abovementioned (4) to bring the concentration up to 1%, the culture medium was filtered with a filter, and the coagulum was eliminated.

(6) Supply of Neurotrophic Factor Group to PC12 Cells, and Neurite Outgrowth

The culture medium of the PC12 cells cultured in a similar manner to that of the abovementioned Experiment 1 was aspirated, and the culture medium filtered via (5) was added to the PC12 cells. Thereafter, the PC12 cells were cultured for 24 hours under a 5% carbon dioxide concentration at 37° C.

As described above, a heated group sample, in which a heated culture medium of the MB8 cells was added to the PC12 cells, was formed from among the magnetically stimulated group. Moreover, an unstimulated group sample in which magnetic stimulation was not applied to the MB8 cells, and an unheated group sample from the magnetically stimulated group in which the heating of the abovementioned (4) was not applied, were formed in a similar manner to that of the abovementioned Experiment 1.

(7) Determination of Neurite Outgrowth in PC12 Cells

Regarding each of the abovementioned unstimulated group, heated group, and unheated group, the number of positive PC12 cells in which neurites were outgrown was counted in a similar manner to that employed by the abovementioned Experiment 1, and the neurite outgrowth ratio (ratio of positive cells) thereof was calculated.

As described above, the experimental conditions and the experimental procedures of the abovementioned Experiment 5 were described. Then, the experimental results of the Experiment 5 will be described with reference to FIG. 10. FIG. 10 is a graph showing the neurite outgrowth ratio of the unstimulated group, the unheated group, and the heated group.

As shown in FIG. 10, the neurite outgrowth ratio of the unstimulated group, the unheated group, and the heated group were 1.1%, 34.4%, and 21.3%, respectively. First, the unstimulated group and the heated group were compared. According to the abovementioned experimental results, it was confirmed that even the heated group altered via the heating of the neurotrophic factor had a neurite outgrowth ratio that was approximately 1.9 times higher (=21.1%/11.1%) than that of the unstimulated group. Moreover, PC12 cells in which the morphology thereof had changed to that of a neural cell were also observed in the heated group. According to these experimental results, the presence of a substance, other than a neurotrophic factor, demonstrating the neurite outgrowth effect was clearly verified. Therefore, the MB8 cells produced, via magnetic stimulation, not only a neurotrophic factor which is protein (thermolabile component) but also a substance demonstrating a neurite outgrowth effect other than these (i.e., a neurotrophic factor-like substance: including thermostable component), and as such, the neurites of the PC12 cells were said to be outgrown via the neurotrophic factor-like substance.

Next, when the unheated group and heated group were compared, the outgrowth ratio of the heated group was approximately 62% that of the unheated group (=21.3%/34.4%). Accordingly, when the neurite outgrowth effect via magnetic stimulation (the outgrowth ratio of the unheated group) was 100%, the neurite outgrowth effect was reduced approximately 38% by heating, as a result of the thermolabite component (i.e., neurotrophic factor and proteinaceous neurotrophic factor-like substance). That is to say, the neurite outgrowth effect via a component (the thermostable component of the neurotrophic factor-like substance) that has not been denatured by heat is approximately 62%. Accordingly, based on the abovementioned experimental results, the presence of a non-proteinaceous component (i.e., neurotrophic factor-like substance) with the proteinaceous component (i.e., neurotrophic factor and proteinaceous neurotrophic factor-like substance) excluded therefrom was verified. However, since not only was the neurotrophic factor, but also a proteinaceous substance other than a neurotrophic factor and a proteolytic enzyme that is a neurite formation inhibitor were denatured by heating, it can not be said for certain that all of the neurite outgrowth effects of the heated group resulted from the non-proteinaceous component. Since there is a variety of types of substances other than the proteinaceous neurotrophic factor and proteolytic enzymes, it is extremely difficult to measure these results and calculate the effects thereof.

According to the abovementioned experimental results, the MB8 cells produced not only, via magnetic stimulation, the neurotrophic factor protein but also the neurotrophic factor-like substance, and the neurites of the PC12 cells can be outgrown by the action of this neurotrophic factor-like substance. Accordingly, via the reception of magnetic stimulation, cells producing a neurotrophic factor of a glial cell and the like were verified as producing, in addition to neurotrophic factor, the neurotrophic factor-like substance demonstrating the neurite outgrowth effect on the central nervous system cells or craniospinal nervous system cells.

As described above, according to an embodiment of the present invention, Experiments 1-5 were described. According to the experimental results mentioned above, it was verified that employing the magnetic treatment device 10 of the present embodiment to apply a high frequency alternating magnetic field of a desired frequency to the cells of an affected area, allows the intracellular concentration of calcium ions to be increased so as to induce the exocytosis of the neurotrophic factor group, and mRNA of the intracellular neurotrophic factor group to be increased so as to promote the synthesis and release of the intracellular neurotrophic group. Moreover, it was verified that by promoting the production of the neurotrophic factor group in such a manner, the production of the neurotrophic factor group of the central nervous system cells or craniospinal nervous system cells is promoted, and the repair, growth, differentiation, or proliferation of these cells is promoted, so that various diseases such as a brain disease can be treated.

Although the preferred embodiments of the present invention have been explained above with reference to the appended drawings, the present invention is not specifically limited to such an example. Thus, so long as one is skilled in the art, it is clear that various alternative embodiments or modified embodiments covered within the scope of the appended claims would be readily apparent, and thus it is understood that all such alternatives and/or modifications are naturally included within the technical scope of the present invention.

For example, although the high frequency and low frequency electromagnetic wave generating means of the abovementioned embodiment include a coil, such as the high frequency coil 30 or the low frequency coil 40 as the antenna emitting the electromagnetic wave, the present invention is not specifically limited to such an example. For example, in addition to a loop antenna, such as a coil or the like, the antenna emitting the electromagnetic wave may also be constructed of various types of antennas, such as a rod antenna, a Hertz dipole antenna, a short antenna, a half-wave dipole antenna, a helical antenna, a monopole antenna, a rhombic antenna, an array antenna, a horn antenna, a parabolic antenna, or a slot antenna. Moreover, the coil employed as the abovementioned antenna may be configured from a solenoid coil, a Helmholtz antenna, a rotary coil, a split pair coil, a shim coil, or a saddle type coil or the like. Furthermore, the material, the shape, the size, the number of turns, the presence or absence of a shaft core, and the location and the like of the high frequency coil 30 and low frequency coil 40 are also not specifically limited to the examples of the abovementioned embodiment (FIG. 2A and FIG. 2B), and as such, design modifications are possible where needed.

Moreover, in the abovementioned embodiment, although a circuit structure such as that of the control block 20 shown in FIG. 3 is employed as the high frequency oscillation means and the low frequency oscillation means applying the high frequency electric current or the low frequency electric current to the high frequency coil 30 or the low frequency coil 40, the present invention is not specifically limited to such an example. For example, so long as the circuit structure of the control block 20 allows for the oscillation of a high frequency wave within the predetermined range of the high frequency for the promotion of production, various design modifications are possible. For example, the high frequency oscillation means 24 that is capable of the oscillation of the abovementioned high frequency wave and the low frequency oscillation means 25 that is capable of the oscillation of the predetermined low frequency wave (e.g., 2.0 kHz, and 7.81 Hz) may be included without the necessity to include a main control circuit composed of a micro-computer and the like.

In addition, although 83.3 MHz or 135 MHz is mainly exemplified as the high frequency for the promotion of production of the high frequency electromagnetic wave (high frequency alternating magnetic field) in the abovementioned embodiments and the Examples, so long as the high frequency for the promotion of production is a predetermined frequency within the range of 20 MHz to 180 MHz, 280 MHz to 600 MHz, or 700 MHz to 1000 MHz (the fourth most preferable range), the present invention is not specifically limited to such an example. Furthermore, although 2.0 kHz is exemplified as the low frequency for the production of promotion of the low frequency electromagnetic wave, it is not specifically limited to such an example, and as such, may include a predetermined frequency within the range of approximately 2.0±10% kHz, or an arbitrary frequency within a range other than this one.

Moreover, although the high frequency electromagnetic wave of the abovementioned embodiment is a substantially sinusoidal wave, it is not specifically limited thereto. For example, a substantially rectangular wave, a saw-tooth wave or the like, may also be included. In addition, although the low frequency electromagnetic wave is a substantially rectangular wave, it is not specifically limited thereto. For example, a substantially sinusoidal wave, a saw-tooth wave or the like, may also be included. In addition, although the abovementioned low frequency electromagnetic wave is a substantially rectangular wave of two values, a positive predetermined value and a zero value, it is not specifically limited to these two values. For example, both values may be positive or negative, or one value may be positive and the other negative, or the like.

Furthermore, although the high frequency electromagnetic wave generating means in the abovementioned embodiment intermittently generates a high frequency electromagnetic wave of a composite frequency of approximately 2.0 kHz and approximately 7.81 Hz, the present invention is not specifically limited thereto. For example, the high frequency electromagnetic wave generating means may also intermittently generate a high frequency electromagnetic wave of a frequency of either approximately 2.0±10% kHz or approximately 7.81±10% Hz alone, or may continuously generate a non-intermittent high frequency electromagnetic wave of at least one frequency other than the abovementioned frequencies.

Moreover, the high frequency electromagnetic wave generating means may not only completely intermittently generate the high frequency electromagnetic wave, but also may generate the high frequency electromagnetic wave so that the electromagnetic wave intensity thereof is sinusoidally increased and decreased at the predetermined at least one frequency (e.g., approximately 2.0±10% kHz and approximately 7.81±10% Hz), for example. Since this also allows the intensity of the high frequency alternating magnetic field applied to the subject to be treated to be periodically increased and decreased, and the stimulation of the alternating magnetic field to be changed, the magnetic treatment effect is enhanced. Furthermore, for example, a low frequency electromagnetic wave generated by the low frequency electromagnetic wave generating means may be periodically increased and decreased or may be interrupted in synchronization with the periodic increases and decreases in the high frequency electromagnetic wave intensity.

In addition, although the low frequency electromagnetic wave generating means of the abovementioned embodiment intermittently generates a low frequency electromagnetic wave at a cycle of approximately 7.81 Hz, the present invention is not specifically limited thereto. For example, the low frequency electromagnetic wave generating means may also intermittently generate a low frequency electromagnetic wave of at least one frequency other than the abovementioned frequencies. Furthermore, the low frequency electromagnetic wave generating means may continuously generate a non-intermittent low frequency electromagnetic wave.

Moreover, although the magnetic treatment device 10 of the abovementioned embodiment is constructed to be capable of generating both a high frequency electromagnetic wave and a low frequency magnetic wave, by including both the high frequency oscillation means 24 and the low frequency oscillation means 25 therein, the present invention is not specifically limited thereto. The magnetic treatment device 10 may also have a structure for solely generating the abovementioned high frequency electromagnetic wave, without including the abovementioned low frequency oscillation means 25. Furthermore, in addition to the abovementioned high frequency oscillation means 24 and/or the abovementioned low frequency oscillation means 25, the magnetic treatment device 10 may additionally include at least one novel electromagnetic wave generating means (e.g., a separate coil). In addition, the electromagnetic wave generated by the additional electromagnetic wave generating means may also be an electromagnetic wave of an arbitrary frequency, such as a long wave, a medium wave, a short wave, an ultra short wave, a microwave.

Moreover, aside from a structural element other than that described above, the magnetic treatment device 10 may also optionally include a vibration generating means for providing vibrations to the subject to be treated; various measuring devices for measuring the frequency or intensity of the electromagnetic wave (alternating magnetic field) to be applied, room temperature, body temperature, amount of battery remaining, and the like; a timer device for automatically activating an on/off mode or the like of an operation, by measuring and controlling the continuous irradiation time of the alternating magnetic field (operation time); a sound generating device, such as a buzzer device for notifying a user via voice of the end of the scheduled treatment time or power consumption; an attaching means, such as a belt or adhesive agent, for attaching the main body of the treatment device on the affected area; and the like.

Furthermore, although the magnetic treatment device 10 of the abovementioned embodiment is configured to generate a high frequency electromagnetic wave of the high frequency for the promotion of production that is selected from the range of 20 MHz to 180 MHz, 280 MHz to 600 MHz, or 700 MHz to 1000 MHz, the present invention is not specifically limited thereto.

For example, the magnetic treatment device 10 may be configured so as to oscillate a frequency in which an arbitrary frequency within the range of the abovementioned high frequency for the promotion of production is divided by an arbitrary positive integer (e.g., approximately 75 MHz, 50 MHz, 37.5 MHz, 30 MHz, . . . , which are 150 MHz divided by the positive integers 2, 3, 4, 5, . . . ), and configured so as to also generate the high frequency electromagnetic wave of the abovementioned high frequency for the promotion of production using a higher harmonic wave that additionally occurs when generating the electromagnetic wave of this frequency.

Specifically, in general, when the fundamental harmonic of the high frequency electromagnetic wave that is generated is not a completely sinusoidal wave, the higher harmonic wave is inevitably generated also for a frequency that is an integral multiple of the fundamental harmonic. FIG. 11 is a graph measuring the distribution of frequency that is actually generated from the magnetic treatment device 10 when the frequency of the high frequency electromagnetic wave generated by the magnetic treatment device 10 of the abovementioned embodiment is set at 80 MHz. As shown in FIG. 11, when the magnetic treatment device 10 that is set at 80 MHz, the high frequency electromagnetic wave of a frequency (e.g., 160 MHz, 240 MHz, 320 MHz, 400 MHz, 480 MHz, . . . ) that is an integral multiple (e.g., 2×, 3×, 4×, . . . ) of 80 MHz is generated as the higher harmonic wave.

So long as the frequency of the higher harmonic wave generated in this manner is within the desired range, for example, 20 MHz to 180 MHz, 280 MHz to 600 MHz, or 700 MHz to 1000 MHz (within the fourth most preferable range), of the high frequency for the promotion of production of the abovementioned embodiment, it is thought that the magnetic treatment effect occurs from the application of the abovementioned higher harmonic wave to the subject to be treated. Accordingly, the magnetic treatment device and the neurotrophic factor production promoting device generating the fundamental harmonic as the generating source of the abovementioned higher harmonic wave are included within the technical scope of the present invention.

In addition, the magnetic treatment device 10 may also generate a high frequency electromagnetic wave of a high frequency for the promotion of production that is within the abovementioned first to fourth most preferable ranges by intermittently generating a high frequency electromagnetic wave of a frequency that is higher than that of the abovementioned first to fourth most preferable ranges (greater than 1000 MHz) with a frequency that is within the abovementioned first to fourth most preferable ranges.

Specifically, even if the living cells of the human body and the like receive the irradiation of an electromagnetic wave of a frequency band of an excessively high frequency, they may not react to changes in the alternating magnetic field of the abovementioned high frequency. By utilizing the insensitivity of the above living cells, a high frequency electromagnetic wave that is higher than that of the abovementioned first to fourth most preferable ranges (e.g., 1 GHz) is generated as a carrier wave, and the abovementioned carrier wave is output by being turned on/off at a cycle corresponding to a frequency within the first to fourth most preferable ranges (e.g., 150 MHz), which is the abovementioned frequency for the production of promotion, to thereby allow the living cells to react as if only an electromagnetic wave of the high frequency wave for the production of promotion was irradiated. Accordingly, the magnetic treatment device and the neurotrophic factor production promoting device that intermittently generate the carrier wave as the generating source of the high frequency wave are included within the technical scope of the present invention.

Moreover, the high frequency for the promotion of production may also be of a fixed value within the abovementioned first to fourth most preferable ranges. However, when the high frequency alternating magnetic field of the same high frequency for the production of promotion is continuously applied to the cells of an affected area, there is a possibility that the cells of the affected area will become accustomed to the above frequency, and thus the magnetic treatment effect will be reduced. Thus, during the treatment employing the abovementioned magnetic treatment device 10 (during the irradiation of the high frequency alternating magnetic field on the affected area), the abovementioned high frequency for the promotion of production may also be changed within the abovementioned first to fourth most preferable ranges. Accordingly, since high frequency alternating magnetic fields of different high frequencies for the promotion of production may be applied to the cells of an affected area during the magnetic treatment, the magnetic stimulation which the cells receive is changed, and the magnetic treatment effect can be enhanced. Moreover, the above-described changes in the high frequency for the promotion of production can be achieved by, for example, changing the frequency of the high frequency electric current applied to the high frequency coil 30 by the high frequency oscillation means within the abovementioned range.

In addition, although an example of the neurotrophic factor production promoting device utilized as the magnetic treatment device 10 for the application of magnetic stimulation to the affected area of a living body was described, the present invention is not specifically limited to such an example. So long as the neurotrophic factor production promoting device of the present invention is a device promoting the production of the neurotrophic factor group by the application of magnetic stimulation to cells, various devices, such as a test device applying magnetic stimulation to cells isolated from the subject to be treated (e.g., human body, or animal), for example, may also be applicable.

Furthermore, the neurotrophic factor and neurotrophic factor-like substance are not specifically limited to the substances illustrated by the abovementioned embodiments. So long as the neurotrophic factor and the neurotrophic factor-like substance of the present invention are substances contributing to the repair, growth, differentiation or proliferation of central nervous system cells or craniospinal nervous system cells, any currently known substances, as well as any substances that may be discovered in the future, may be included therein.

INDUSTRIAL APPLICABILITY

The present invention is applicable to a production promoting device for an intracellular neurotrophic factor group, specifically it is applicable to a magnetic treatment device for treating a neurodegenerative disorder such as Alzheimer's disease, depression, or the like.

The invention claimed is:
1. A device configured to promote the production of a neurotrophic factor via application of magnetic stimulation to cells, the device comprising:
   a high frequency electromagnetic wave generating means generating a high frequency electromagnetic wave of a high frequency for promotion of production selected from the range of 20 MHz to 180 MHz, 280 MHz to 600 MHz, or 700 MHz to 1000 MHz and comprising a high frequency coil that generates the high frequency electromagnetic wave,
   a low frequency electromagnetic wave generating means generating a low frequency electromagnetic wave lower than the high frequency electromagnetic wave and comprising a low frequency coil that generates the low frequency electromagnetic wave and wherein the low frequency coil is different from the high frequency coil; and
   a frequency controlling means that generates the high and low frequency electromagnetic waves intermittently.
2. The device of claim 1, wherein the high frequency for the promotion of production is selected from the range of 60 MHz to 180 MHz, 280 MHz to 300 MHz, 450 MHz to 550 MHz, or 900 MHz to 950 MHz.

3. The device of claim 1, wherein the high frequency for the promotion of production is selected from the range of 100 MHz to 160 MHz.

4. The device of claim 1, wherein the high frequency for the promotion of production is selected from the range of 120 MHz to 160 MHz.

5. The device of claim 1, wherein the high frequency electromagnetic wave generating means includes, further comprises
- a high frequency oscillation means outputting a high frequency electric current; and
- a high frequency antenna generating the high frequency electromagnetic wave of the high frequency for the promotion of production via application of a high frequency current from the high frequency oscillation means.

6. The device of claim 1, wherein the high frequency electromagnetic wave generating means intermittently generates the high frequency electromagnetic wave, by repeating an on time period in which the high frequency electromagnetic wave is generated and an off time period in which the high frequency electromagnetic wave is not generated, at a predetermined cycle.

7. The device of claim 6, wherein the high frequency electromagnetic wave generating means intermittently generates the high frequency electromagnetic wave, by repeating a first on time period in which the high frequency electromagnetic wave is generated and a first off time period in which the high frequency electromagnetic wave is not generated, at a cycle corresponding to 2.0±10% kHz.

8. The device of claim 6, wherein the high frequency electromagnetic wave generating means intermittently generates the high frequency electromagnetic wave, by repeating a second on time period in which the high frequency electromagnetic wave is generated and a second off time period in which the high frequency electromagnetic wave is not generated, at a cycle corresponding to 7.8±10% Hz.

9. The device of claim 1, wherein the low frequency electromagnetic wave generating means further comprises
- a low frequency oscillation means outputting a low frequency electric current; and
- a low frequency antenna generating the low frequency electromagnetic wave of the low frequency for the promotion of production via application of a low frequency current from the low frequency oscillation means.

10. The device of claim 9, wherein a rise time of the low frequency electric current applied to the low frequency antenna is no more than 0.1 μsec.

11. The device of claim 1, wherein the low frequency electromagnetic wave generating means intermittently generates the low frequency electromagnetic wave, by repeating an on time period in which the low frequency electromagnetic wave is generated and an off time period in which the low frequency electromagnetic wave is not generated, at a predetermined cycle.

12. The device of claim 11, wherein the low frequency electromagnetic wave generating means intermittently generates the low frequency electromagnetic wave, by repeating a third on time period in which the low frequency electromagnetic wave is generated and a third off time period in which the low frequency electromagnetic wave is not generated, at a cycle corresponding to 7.8±10% Hz.

13. The device of claim 11, wherein
- the high frequency electromagnetic wave generating means intermittently generates the high frequency electromagnetic wave, by repeating an on time period in which the high frequency electromagnetic wave is generated and an off time period in which the high frequency electromagnetic wave is not generated, at a predetermined cycle, and
- the on time period of the high frequency electromagnetic wave and the on time period of the low frequency electromagnetic wave are synchronized with each other.

14. The device of claim 1, wherein the low frequency electromagnetic wave generating means generates a low frequency electromagnetic wave in the range of 2.0±10% kHz.

15. A method for promoting neurotrophic factor production in a cell, the method comprising applying magnetic stimulation to the cells with the device of claim 1, wherein
- the magnetic stimulation by the high frequency alternating magnetic field of the high frequency is configured and suitable for increasing a concentration of calcium ions within the cells so that exocytosis of the neurotrophic factor is induced, and the magnetic stimulation increases synthesis of messenger ribonucleic acid (mRNA) of the neurotrophic factor in the cells so that the synthesis and extracellular release of the neurotrophic factor increases.

* * * * *